US011878000B2

(12) United States Patent
Yin et al.

(10) Patent No.: US 11,878,000 B2
(45) Date of Patent: *Jan. 23, 2024

(54) COMPOUNDS AND METHODS TO SENSITIZE CANCER CELLS TO TYROSINE KINASE INHIBITORS

(71) Applicants: Cedars-Sinai Medical Center, Los Angeles, CA (US); Da Zen Theranostics, Inc., Beverly Hills, CA (US)

(72) Inventors: Liyuan Yin, Los Angeles, CA (US); Yi Zhang, Los Angeles, CA (US); Stefan Mrdenovic, Osijek (HR); Gina Chia Yi Chu, Los Angeles, CA (US); Ruoxiang Wang, Los Angeles, CA (US); Qinghua Zhou, Chengdu (CN); Jian Zhang, Ann Arbor, MI (US); Leland W. K. Chung, Beverly Hills, CA (US)

(73) Assignees: Da Zen Theranostics, Inc., San Jose, CA (US); Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/343,645

(22) PCT Filed: Oct. 21, 2017

(86) PCT No.: PCT/US2017/057761
§ 371 (c)(1),
(2) Date: Apr. 19, 2019

(87) PCT Pub. No.: WO2018/075993
PCT Pub. Date: Apr. 26, 2018

(65) Prior Publication Data
US 2019/0269783 A1 Sep. 5, 2019

Related U.S. Application Data

(60) Provisional application No. 62/410,960, filed on Oct. 21, 2016.

(51) Int. Cl.
| | |
|---|---|
| *A61K 31/395* | (2006.01) |
| *A61K 31/404* | (2006.01) |
| *A61P 35/00* | (2006.01) |
| *A61K 31/22* | (2006.01) |
| *A61K 31/282* | (2006.01) |

(Continued)

(52) U.S. Cl.
CPC ........... *A61K 31/404* (2013.01); *A61K 31/22* (2013.01); *A61K 31/282* (2013.01); *A61K 31/337* (2013.01); *A61K 31/351* (2013.01); *A61K 31/357* (2013.01); *A61K 31/366* (2013.01); *A61K 31/40* (2013.01); *A61K 31/4045* (2013.01); *A61K 31/47* (2013.01); *A61K 31/505* (2013.01); *A61K 31/513* (2013.01); *A61K 31/519* (2013.01); *A61K 31/5377* (2013.01); *A61K 31/555* (2013.01); *A61K 31/65* (2013.01); *A61K 31/704* (2013.01); *A61K 31/7068* (2013.01); *A61K 33/243* (2019.01); *A61K 47/52* (2017.08); *A61K 47/545* (2017.08); *A61K 47/55* (2017.08); *A61K 49/0004* (2013.01); *A61K 49/0032* (2013.01); *A61P 35/00* (2018.01); *A61P 35/04* (2018.01); *C07D 209/10* (2013.01); *C07D 405/14* (2013.01);

(Continued)

(58) Field of Classification Search
CPC .................................................. A61K 31/395
See application file for complete search history.

(56) References Cited

U.S. PATENT DOCUMENTS

| | | | |
|---|---|---|---|
| 6,376,537 | B1 | 4/2002 | Weinberg |
| 7,198,778 | B2 | 4/2007 | Achilefu et al. |

(Continued)

FOREIGN PATENT DOCUMENTS

| | | |
|---|---|---|
| CN | 104312194 A | 1/2015 |
| WO | 2009152440 A1 | 12/2009 |

(Continued)

OTHER PUBLICATIONS

National Cancer Institute. "Erlotinib Hydrochloride." (Oct. 5, 2006). Accessed Jul. 4, 2020. Available from: < https://www.cancer.gov/about-cancer/treatment/drugs/erlotinibhydrochloride >. (Year: 2006).*

(Continued)

*Primary Examiner* — John S Kenyon
(74) *Attorney, Agent, or Firm* — McCarter & English, LLP; Michael J. DeGrazia

(57) ABSTRACT

The present invention generally relates to sensitizer compounds and their use in combination with Tyrosine Kinase Inhibitors (TKIs) for sensitizing tumor, cancer or pre-cancerous cells to TKI treatment. In particular, the present invention relates to administration regimes that combine TKIs such as Gefitinib or Icotinib with TKI-sensitizing DZ1 esters and amides conjugated to statin or platin-based drugs, or to Artemisinin, including, without limitation: DZ1-Simvastatin amide, DZ1-Simvastatin ester, DZ1-Cisplatin ester, and DZ1-Cisplatin amide, DZ1-Artemisinin ester, and DZ1-Artemisinin amide. Furthermore, the present invention relates to improved TKI treatment of cancers by sensitizing tumor, cancer or pre-cancerous cells, in particular cancers that develop TKI resistance, including e.g. lung cancer and pancreatic cancer.

21 Claims, 8 Drawing Sheets

(51) Int. Cl.

| | | |
|---|---|---|
| *A61K 31/337* | (2006.01) | |
| *A61K 31/351* | (2006.01) | |
| *A61K 31/366* | (2006.01) | |
| *A61K 31/47* | (2006.01) | |
| *A61K 31/513* | (2006.01) | |
| *A61K 47/54* | (2017.01) | |
| *A61P 35/04* | (2006.01) | |
| *A61K 33/243* | (2019.01) | |
| *A61K 31/357* | (2006.01) | |
| *A61K 31/519* | (2006.01) | |
| *A61K 31/5377* | (2006.01) | |
| *A61K 31/65* | (2006.01) | |
| *A61K 47/55* | (2017.01) | |
| *A61K 47/52* | (2017.01) | |
| *A61K 31/4045* | (2006.01) | |
| *A61K 31/505* | (2006.01) | |
| *A61K 31/555* | (2006.01) | |
| *A61K 31/704* | (2006.01) | |
| *A61K 31/7068* | (2006.01) | |
| *A61K 49/00* | (2006.01) | |
| *C07D 493/18* | (2006.01) | |
| *C07D 209/10* | (2006.01) | |
| *C07D 405/14* | (2006.01) | |
| *A61K 31/40* | (2006.01) | |
| *C09B 23/01* | (2006.01) | |
| *A61K 45/06* | (2006.01) | |

(52) U.S. Cl.
CPC ........ *C07D 493/18* (2013.01); *C09B 23/0016* (2013.01); *C09B 23/0066* (2013.01); *A61K 45/06* (2013.01)

(56) References Cited

U.S. PATENT DOCUMENTS

| | | | |
|---|---|---|---|
| 9,771,625 B2 | 9/2017 | Shih et al. | |
| 10,307,489 B2* | 6/2019 | Chung | ............... A61P 35/00 |
| 2002/0151583 A1 | 10/2002 | Weinberg | |
| 2003/0232033 A1 | 12/2003 | Cantrell | |
| 2012/0219570 A1 | 8/2012 | Chang et al. | |
| 2013/0039854 A1 | 2/2013 | Shih et al. | |
| 2013/0101513 A1 | 4/2013 | Yang et al. | |
| 2014/0248213 A1 | 9/2014 | Chung et al. | |
| 2014/0323551 A1 | 10/2014 | Chung et al. | |
| 2015/0209361 A1 | 7/2015 | Shih et al. | |
| 2019/0262312 A1* | 8/2019 | Yin | ............... A61K 31/4045 |
| 2019/0269783 A1 | 9/2019 | Yin et al. | |
| 2019/0269801 A1* | 9/2019 | Chung | ............ C09B 23/0016 |
| 2022/0031855 A1* | 2/2022 | Chung | ............ C09B 23/0066 |
| 2023/0116399 A1* | 4/2023 | Chung | ............ C07D 405/14 |
| | | | 514/460 |

FOREIGN PATENT DOCUMENTS

| | | | |
|---|---|---|---|
| WO | 2013016580 A2 | 1/2013 | |
| WO | WO-2013052776 A1 * | 4/2013 | ......... C09B 23/0066 |
| WO | 2014086942 A1 | 6/2014 | |
| WO | 2015188934 A1 | 12/2015 | |
| WO | WO-2016106324 A1 * | 6/2016 | ............. A61P 35/00 |
| WO | 2018075993 A1 | 4/2018 | |
| WO | 2018075994 A1 | 4/2018 | |
| WO | 2018075996 A1 | 4/2018 | |

OTHER PUBLICATIONS

"Kinase Inhibitors for Cancer Treatment—Chemotherapy." (Apr. 24, 2010). Accessed Jul. 5, 2020. Available from: < https://chemoth.com/types/kinaseinhibitors >. (Year: 2010).*
Partial European Supplementary Search Report from European Patent Application No. 17862099.3 dated Sep. 1, 2020.
Boyang Wu et al., "Near-Infrared fluorescence heptamethine carbocyanine dyes mediate imaging and targeted drug delivery for human brain tumor," Biomaterials, Oct. 1, 2015, vol. 67, pp. 1-10.
Boyang Wu et al., "Supplementary Data Near-Infrared Fluorescence Heptamethine Carbocyanine Dyes Mediate Imaging and Targeted Drug Delivery for Human Brain Tumor," Appendix A, Oct. 1, 2015, https://ars.els-cdn.com/ content/image/1-s2.0-S0142961215006109-mmc1.pdf.
Yang Guan et al., "Improving Therapeutic Potential of Farnesylthiosalicylic Acid: Tumor Specific Delivery via Conjugation with Heptamethine Cyanine Dye," Molecular Pharmaceutics, Mar. 21, 2016, vol. 14, No. 1, pp. 1-13.
Ki-Eun Hwang et al., "Effect of simvastatin on the resistance of EGFR tyrosine kinase inhibitors in a non-small cell ung cancer with the T790M mutation of EGFR," Experimental Cell Research, May 1, 2014, vol. 323, No. 2, pp. 288-296.
Partial European Supplementary Search Report from European Patent Application No. 17862097.7 dated May 27, 2020.
Wu et al., Near-Infrared Fluorescence and nuclear imaging and targeting of prostate cancer, Trans. Androl. Urol. 2013, 2, 254-264.
Zhang, E. et al., "Mechanistic study of IR-780 dye as a potential tumor targeting and drug delivery agent," Biomaterials, Jan. 2014, vol. 35, No. 2, pp. 771-778, p. 776, FIG 5A, p. 777, 3.5.
Yang, Z. et al., "Folate-based near-infrared fluorescent theranostic gemcitabine delivery," J. Am. Chem. Soc., Aug. 7, 2013, vol. 135, No. 31, pp. 11657-11662.
Xiao, L. et al., Heptamethine cyanine based (64)Cu-PET probe PC-1001 for cancer imaging: synthesis and in vivo evaluation, Nucl. Med. Biol., Apr. 2013, vol. 40, No. 3, pp. 351-360.
International Search Report published with WO2016106324 (PCT/US2015/067393).
International Search Report published with WO2018075994 (PCT/US2017/057762).
International Search Report published with WO2018075996 (PCT/US2017/057765).
International Search Report published with WO2018075993 (PCT/US2017/057761).
Partial Supplementary European Search Report from European Patent Application No. 17861447.5, dated Jan. 25, 2021.
Supplemental European Search Report dated May 28, 2021 for European Patent Application No. 17861447.5.

* cited by examiner

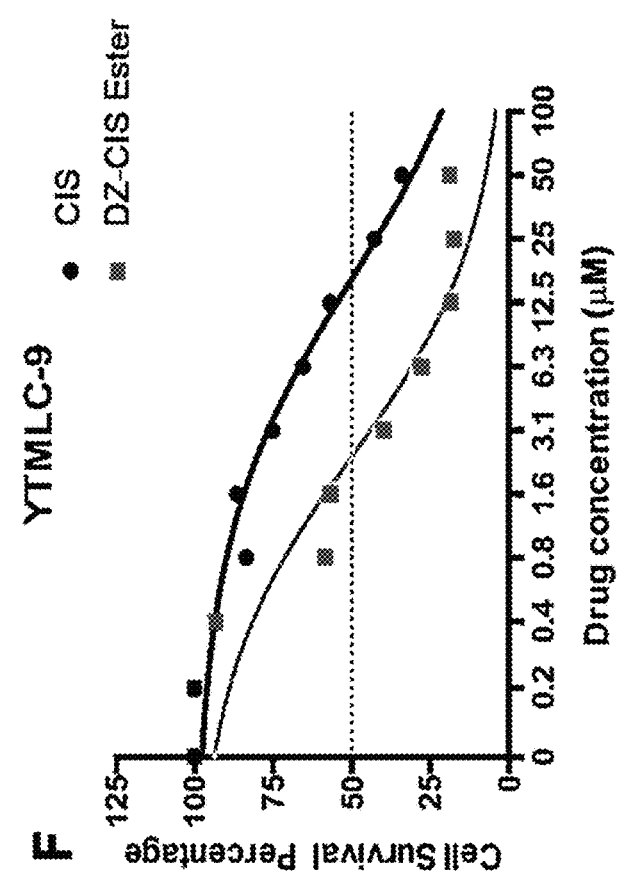
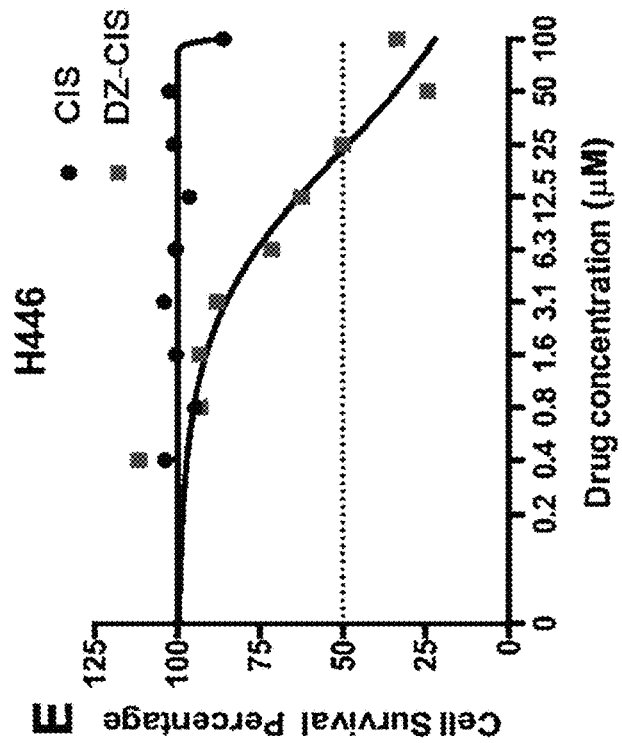
FIG. 1B-2

COMPOUNDS AND METHODS TO SENSITIZE CANCER CELLS TO TYROSINE KINASE INHIBITORS

CROSS-REFERENCE TO RELATED APPLICATIONS

This is an application filed under 35 USC § 371 of PCT/US2017/057761, filed on Oct. 21, 2017, claiming priority to U.S. 62/410,960, filed on Oct. 21, 2016, each of which is herein incorporated by reference in its entirety.

FIELD OF THE INVENTION

The present invention generally relates to sensitizer compounds and their use in combination with Tyrosine Kinase Inhibitors (TKIs) for sensitizing tumor, cancer or pre-cancerous cells to TKI treatment. In particular, the present invention relates to drug administration regimes that combine TKIs such as Gefitinib or Icotinib with TKI-sensitizing DZ1 esters and amides conjugated to statin or platin-based drugs, or to Artemisinin, including, without limitation: DZ1-Simvastatin amide, DZ1-Simvastatin ester, DZ1-Cisplatin ester, and DZ1-Cisplatin amide, DZ1-Artemisinin ester, and DZ1-Artemisinin amide. Furthermore, the present invention relates to improved TKI treatment of cancers by sensitizing tumor, cancer or pre-cancerous cells, in particular cancers that develop TKI resistance, including e.g. lung cancer pancreatic cancer, and kidney cancer.

BACKGROUND OF THE INVENTION

Presently known strategies for cancer therapy employ various combinations to increase sensitivity of cancer cells to chemotherapeutic drugs and/or overcoming resistance to such drugs. These include statins such as simvastatin combined with various therapeutic agents to overcome therapeutic resistance to various tyrosine kinase inhibitors. However, known approaches often lack sufficient effect, benefits may be limited to specific cancer cell phenotypes, and/or studies show inconsistent effectiveness with only some patients benefiting, and others even showing worse outcomes.

Near infrared (NIR) dye cancer drug conjugates are generally known to preferentially target some cancer drugs to cancer cells. However, NIR dye conjugates have not been known to consistently increase sensitivity of cancer cells to TKIs, or to overcome therapeutic resistance to TKIs. Further, increasing the sensitivity of lung, pancreatic and kidney cancer cells, or overcoming their TKI resistance, has not been possible with prior art methods.

Therefore, there is a need in the art for drugs, their formulations and methods that increase the sensitivity of cancer cells to TKI chemotherapeutic drugs. Additionally, there is a need for drugs and methods that allow to overcome TKI resistance in cancer cells. Further, there is a need for drugs and methods that overcome TKI resistance in lung and pancreatic cancer cells. These and other features and advantages of the present invention will be explained and will become obvious to one skilled in the art through the summary of the invention that follows.

SUMMARY OF THE INVENTION

Surprisingly it has been found that certain NIR dye conjugates, in particular certain DZ1-drug ester and amide conjugates, have a cancer cell sensitizing effect when combined with TKIs, and when applied in combination with a TKI, can reduce the necessary TKI dose, and/or overcome cellular TKI resistance. Thus, the present invention generally relates to sensitizer compounds and their use in combination with Tyrosine Kinase Inhibitors (TKIs) for sensitizing tumor, cancer or pre-cancerous cells to TKI treatment. In particular, the present invention relates to drug administration regimes that combine TKIs such as Gefitinib or Icotinib with TKI-sensitizing DZ1 esters and amides conjugated to statin drugs, platin-based drugs or Artemisinin (ART), including, without limitation: DZ1-Simvastatin amide, DZ1-Simvastatin ester, DZ1-Cisplatin ester, DZ1-Cisplatin amide, DZ1-ART ester, and DZ1-ART amide. Furthermore, the present invention relates to improved TKI treatment of cancers by sensitizing tumor, cancer or pre-cancerous cells, in particular cancers that develop TKI resistance, including e.g. lung cancer pancreatic cancer, and kidney cancer.

Embodiments of the invention provide a sensitizer compound which is a DZ1-drug amide or ester conjugate, wherein the drug residue is selected from the group consisting of a statin drug, a platin-based anti-neoplastic drug, and Artemisinin, and the DZ1 residue is selected from an amide and an ester-linked residue shown in formulae I and II below:

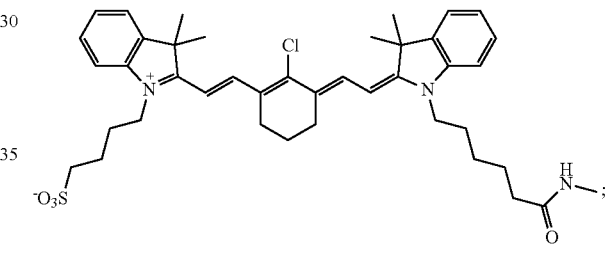

FI

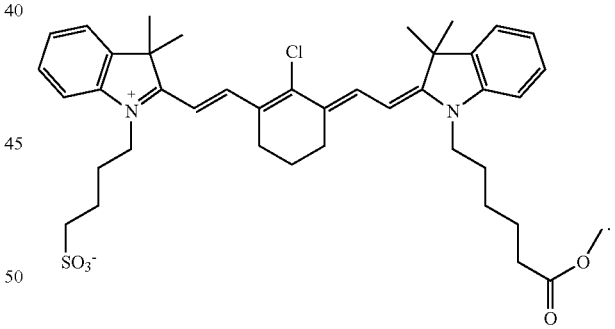

FII

Embodiments of the invention provide drug-conjugate sensitizer compounds wherein the drug is a statin selected from the group consisting of simvastatin (SIM), atorvastatin, fluvastatin, lovastatin, pitavastatin, pravastatin, and rosuvastatin.

Embodiments of the invention provide drug-conjugate sensitizer compounds wherein the drug is a platin-based anti-neoplastic drug selected from the group consisting of cisplatin (CIS), carboplatin (also known as CBDCA), and dicycloplatin (also known as DCP), oxaliplatin, satraplatin, picoplatin, nedaplatin, triplatin, lobapatin, heptaplatin, and lipoplatin.

Embodiments of the invention provide drug-conjugate sensitizer compounds wherein the drug is selected from an ester- or amide-conjugated Simvastatin (SIM), Cisplatin (CIS), and Artemisinin (ART).

Embodiments of the invention provide pharmaceutical compositions comprising a sensitizer compound and at least one pharmaceutically acceptable carrier, wherein the drug residue is selected from the group consisting of a statin drug, a platin-based anti-neoplastic drug, and Artemisinin, and wherein the DZ1 residue is selected from an amide and an ester-linked residue shown in formulae I and II above.

Embodiments of the invention provide pharmaceutical compositions wherein the concentration of the sensitizer compound and its carrier are adapted to deliver the sensitizer to tumor, cancer or pre-cancerous cells of a TKI associated tumor in sufficient concentration to sensitize the cells against a TKI.

Embodiments of the invention provide pharmaceutical compositions as part of a kit of one or more pharmaceutical composition, the kit comprising (1) the sensitizer compound, (2) a tyrosine kinase inhibitor (TKI), (3) one or more delivery means for (1), (2), or for both, and (4) instructions for coordinated administration of the sensitizer compound and the TKI in a common administration regimen, wherein the sensitizer compound is selected from the group consisting of a statin, a platin-based anti-neoplastic drug, and Artemisinin.

Embodiments of the invention provide pharmaceutical compositions as part of a kit wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

Embodiments of the invention provide pharmaceutical compositions as part of a kit wherein the TKI is selected from the group consisting of Gefitinib and Icotinib, and the sensitizer compound is selected from the group consisting of DZ1-SIM ester, DZ1-SIM amide, DZ1-CIS ester, DZ1-CIS amide, DZ1-ART ester, and DZ1-ART amide.

Embodiments of the invention provide a method of sensitizing cancer or precancerous cells present in a subject to treatment with a tyrosine kinase inhibitor (TKI), the method comprising administering to a subject in need of TKI treatment: a) a TKI in an amount and concentration sufficient to cause a cancer cell growth inhibiting and/or apoptosis-inducing TKI effect when administered to the subject together with, or in presence of, one or more sensitizer compound; and b) a sensitizer compound, in an amount and concentration sufficient to provide cancer cell sensitivity to the tyrosine kinase inhibitor, thus allowing for an enhanced effect of the TKI compared to a TKI administered in absence of the sensitizer compound; wherein the sensitizer compound is a DZ1-drug amide or ester conjugate comprising a drug residue, wherein the drug residue is selected from the group consisting of a statin, a platin-based anti-neoplastic drug, and Artemisinin, and wherein the DZ1 residue is selected from an amide and an ester-linked residue shown in formulae FI and FII above.

Embodiments of the invention provide a method of sensitizing cancer or precancerous cells wherein the drug is a statin selected from the group consisting of simvastatin (SIM), atorvastatin, fluvastatin, lovastatin, pitavastatin, pravastatin, and rosuvastatin.

Embodiments of the invention provide a method of sensitizing cancer or precancerous cells wherein the drug is a platin-based anti-neoplastic drug selected from the group consisting of cisplatin (CIS), carboplatin (also known as CBDCA), and dicycloplatin (also known as DCP), oxaliplatin, satraplatin, picoplatin, nedaplatin, triplatin, lobapatin, heptaplatin, and lipoplatin.

Embodiments of the invention provide a method of sensitizing cancer or precancerous cells wherein the drug is selected from an ester- or amide-conjugated Simvastatin (SIM), Cisplatin (CIS), and Artemisinin (ART).

Embodiments of the invention provide a method of sensitizing cancer or precancerous cells wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

Embodiments of the invention provide a method of sensitizing cancer or precancerous cells wherein the tyrosine kinase inhibitor is selected from the group consisting of Gefitinib and Icotinib.

Embodiments of the invention provide a method of sensitizing cancer or precancerous cells by administering to a subject in need of TKI treatment one or more combination of a TKI and a sensitizer selected from the group consisting of: a) Gefitinib in combination with a DZ1-SIM ester sensitizer; b) Gefitinib in combination with a DZ1-SIM amide sensitizer; c) Gefitinib in combination with a DZ1-CIS ester sensitizer; d) Gefitinib in combination with a DZ1-CIS amide sensitizer, Gefitinib in combination with a DZ1-ART ester sensitizer, and/or Gefitinib in combination with a DZ1-ART amide sensitizer.

Embodiments of the invention provide a method of sensitizing cancer or precancerous cells by administering to a subject in need of TKI treatment one or more combination of a TKI and a sensitizer selected from the group consisting of: a) Icotinib in combination with a DZ1-SIM ester sensitizer; b) Icotinib in combination with a DZ1-SIM amide sensitizer; c) Icotinib in combination with a DZ1-CIS ester sensitizer; d) Icotinib in combination with a DZ1-CIS amide sensitizer, Icotinib in combination with a DZ1-ART ester sensitizer, and/or Icotinib in combination with a DZ1-ART amide sensitizer.

Embodiments of the invention provide a method of sensitizing cancer or precancerous cells by administering to a subject in need of TKI treatment one or more TKI selected from the group consisting of Gefitinib, Icotinib, Erlotinib, Afatinib, Brigatinib, Osimertinib, Dacomitinib, Everolimus, and Lapatinib, in combination with or presence of a sensitizer compound selected from the group consisting of: a) a DZ1-SIM ester sensitizer; b) a DZ1-SIM amide sensitizer; c) a DZ1-CIS ester sensitizer; d) a DZ1-CIS amide sensitizer; e) DZ1-ART ester sensitizer and f) DZ1-ART amide sensitizer, or a combination thereof.

Embodiments of the invention provide a method of sensitizing cancer or precancerous cells wherein the cancer or precancerous cells are selected from cells of one or more of lung cancer, NSCLC, SCLC, pancreatic cancer, kidney cancer, colorectal cancer, prostate cancer, skin cancer, HCC cancer, and breast cancer, squamous-cell carcinoma of the lung, anal cancers, glioblastoma, and epithelian tumors of the head and neck.

Embodiments of the invention provide a method of sensitizing cancer or precancerous cells wherein the method further comprises one or more step of identifying, imaging and localizing the sensitized cells by DZ1-fluorescence.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

FIG. 1A-1(A) illustrates the calculated 50% inhibitory concentration (IC50) of DZ1-SIM ester and amide, compared to Simvastatin as tested in cell line A549. FIG. 1A-1(B) illustrates the calculated 50% inhibitory concentration (IC50) of DZ1-SIM ester and amide, compared to Simvastatin as tested in cell line A549/DDP. FIG. 1A-1(C) illustrates the calculated 50% inhibitory concentration (IC50) of DZ1-SIM ester and amide, compared to Simvastatin as tested in cell line 95C. FIG. 1A-1(D) illustrates the calculated 50% inhibitory concentration (IC50) of DZ1-SIM ester and amide, compared to Simvastatin as tested in cell line 95D. FIG. 1A-2(E) illustrates the calculated 50% inhibitory concentration (IC50) of DZ1-SIM ester and amide, compared to Simvastatin as tested in cell line YTMLC-9. FIG. 1A-2(F) illustrates the calculated 50% inhibitory concentration (IC50) of DZ1-SIM ester and amide, compared to Simvastatin as tested in cell line H446. FIG. 1B-1(A) illustrates the calculated 50% inhibitory concentration (IC50) of DZ-CIS ester compared to Cisplatin as tested in cell line A549. FIG. 1B-1(B) illustrates the calculated 50% inhibitory concentration (IC50) of DZ-CIS ester compared to Cisplatin as tested in cell line A549/DDP. FIG. 1B-1(C) illustrates the calculated 50% inhibitory concentration (IC50) of DZ-CIS ester compared to Cisplatin as tested in cell line 95C. FIG. 1B-1(D) illustrates the calculated 50% inhibitory concentration (IC50) of DZ-CIS ester compared to Cisplatin as tested in cell line 95D. FIG. 1B-2(E) illustrates the calculated 50% inhibitory concentration (IC50) of DZ-CIS ester compared to Cisplatin as tested in cell line H446. FIG. 1B-2(F) illustrates the calculated 50% inhibitory concentration (IC50) of DZ-CIS ester compared to Cisplatin as tested in cell line YTMLC-9.

FIG. 2A illustrates the calculated 50% inhibitory concentration (IC50) of DZ1-SIM Amide with various concentrations of Tyrosine Kinase Inhibitor drug, Gefitinib, as tested in cell line H1975. FIG. 2B illustrates the calculated 50% inhibitory concentration (IC50) of DZ1-SIM Amide with various concentrations of Tyrosine Kinase Inhibitor drug, Icotinib, as tested in cell line H1975. FIG. 2C illustrates the calculated 50% inhibitory concentration (IC50) of DZ1-SIM Amide with various concentrations of Tyrosine Kinase Inhibitor drug, Gefitinib, as tested in cell line H1650. FIG. 2D illustrates the calculated 50% inhibitory concentration (IC50) of DZ1-SIM Amide with various concentrations of Tyrosine Kinase Inhibitor drug, Icotinib, as tested in cell line H1650.

FIG. 5 (Top Right) illustrates the calculated 50% inhibitory concentration (IC50) of Tyrosine Kinase Inhibitor drug, Gefitinib, with various concentrations of Gamma-secretase inhibitor RO492909, as tested in cell line A549/DDP. FIG. 5 (Bottom Left) illustrates the calculated 50% inhibitory concentration (IC50) of Tyrosine Kinase Inhibitor drug, Gefitinib, with various concentrations of Gamma-secretase inhibitor RO492909, as tested in cell line H1975. FIG. 5 (Bottom Right) illustrates the calculated 50% inhibitory concentration (IC50) of Tyrosine Kinase Inhibitor drug, Icotinib, with various concentrations of Gamma-secretase inhibitor RO492909, as tested in cell line H1975.

DETAILED DESCRIPTION OF THE INVENTION

Figures 1, 1A:
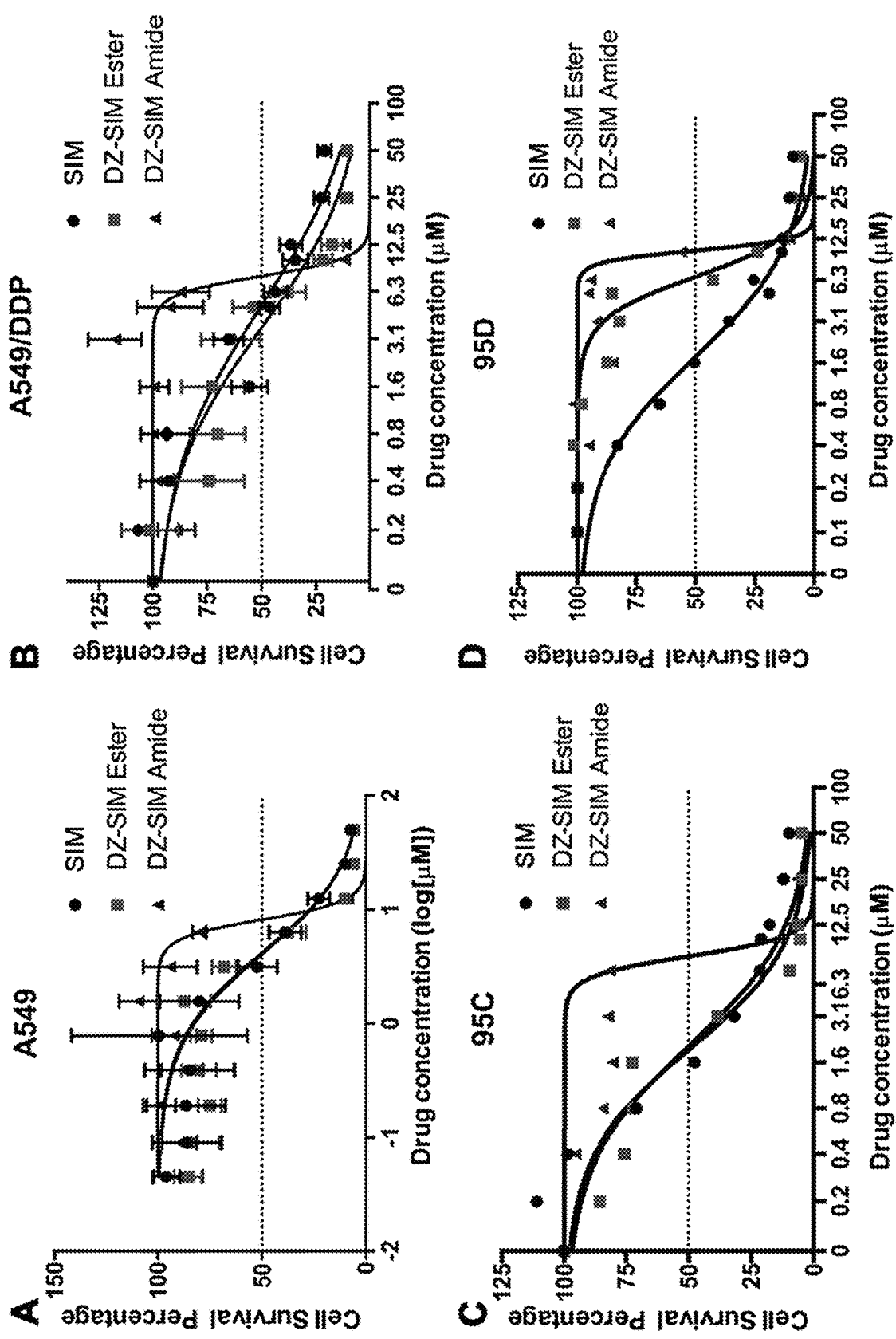

The present invention generally relates to sensitizer compounds and their use in combination with Tyrosine Kinase Inhibitors (TKIs) for sensitizing tumor, cancer or pre-cancerous cells to TKI treatment. In particular, the present invention relates to drug administration regimes that combine TKIs such as Gefitinib or Icotinib with TKI-sensitizing DZ1 esters and amides conjugated to statin drugs, platin-based drugs, or to Artemisinin, including, without limitation: DZ1-Simvastatin amide, DZ1-Simvastatin ester, DZ1-CIS ester, DZ1-CIS amide, DZ1-ART ester, and DZ1-ART amide. Furthermore, the present invention relates to improved TKI treatment of cancers by sensitizing tumor, cancer or pre-cancerous cells, in particular cancers that develop TKI resistance, including e.g. lung cancer pancreatic cancer, and kidney cancer.

According to an embodiment of the present invention, a sensitizer compound, i.e. a DZ1-Drug amide or ester conjugate as herein described, is administered in combination with a tyrosine kinase inhibitor (TKI), in particular a TKI that inhibits the catalytic activity of the epidermal growth factor receptor (EGFR). A TKI is a pharmaceutical drug that inhibits tyrosine kinases. Tyrosine kinases are enzymes responsible for the activation of many proteins by signal transduction cascades, in particular EGFR. The proteins are activated by adding a phosphate group to the protein (phosphorylation), a step that TKIs inhibit. TKIs are typically used as anticancer drugs against various cancers to inhibit the growth of the cancer cells (and stop or slow down tumor growth), and/or to induce the cells to undergo apoptosis (cell death), typically resulting in tumor shrinkage.

According to an embodiment of the present invention, the TKI may include one or more of Gefitinib, Icotinib, Erlotinib, Afatinib, Brigatinib, Osimertinib, Dacomitinib, Everolimus, Lapatinib, Cabozantinib, Sunitinib, and Vandetanib.

According to an embodiment of the present invention, the EGFR Tyrosine Kinase Inhibitor drug (TKI) may include one or more of Gefitinib, Icotinib, Erlotinib, Afatinib, Brigatinib, Osimertinib, Dacomitinib and Lapatinib (a mixed EGFR and ERBB2 inhibitor). Preferred TKIs may be EGFR TKIs, and Gefitinib and Icotinib, or combinations thereof, are particularly preferred.

According to an embodiment of the present invention, tumor, cancer or pre-cancerous cells of a subject may be exposed to one of more sensitizer compound, e.g. by administering the sensitizer to a patient in need of treatment for a cancer that involves TKI, in particular cancers that are susceptible to develop TKI resistant, including TKI resistant cancers that already developed resistance, e.g. after therapy with one or more TKI.

According to an embodiment of the present invention, the DZ1-conjugated sensitizers may include DZ1-CIS ester, DZ1-CIS amide, DZ1-SIM ester, and DZ1-SIM amide, DZ1-ART ester, and DZ1-ART amide, and their use for sensitizing tumor, cancer or pre-cancerous cells to treatment with TKIs by exposing such cells to the sensitizer and the TKI, e.g. by administering a sensitizers and a TKI to a subject having such cells, including cancer and tumor patients. Particular examples of these sensitizers and their chemical formulae are shown below. The sensitizers include

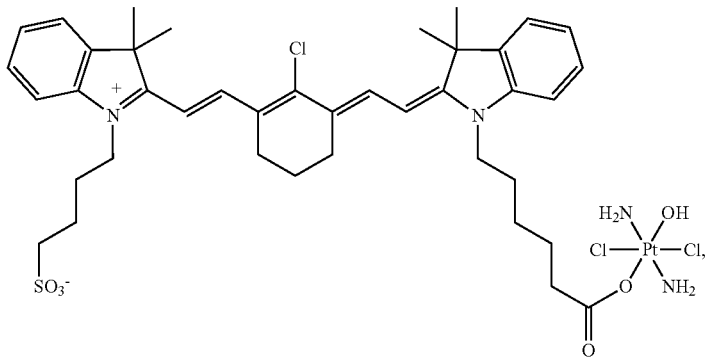

DZ1-CIS ester

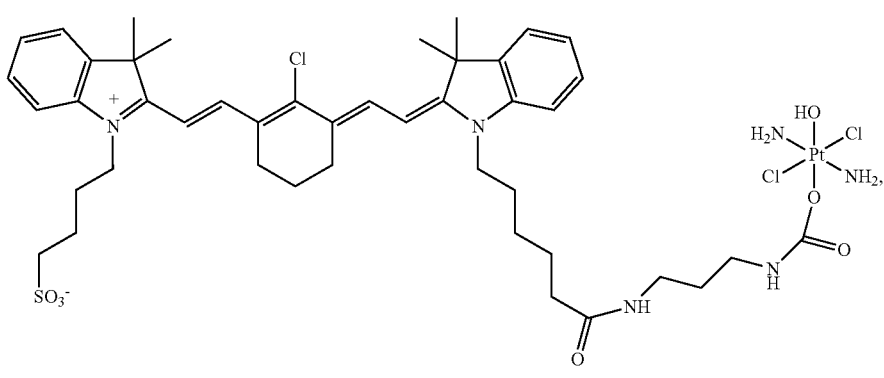

DZ1-CIS amide

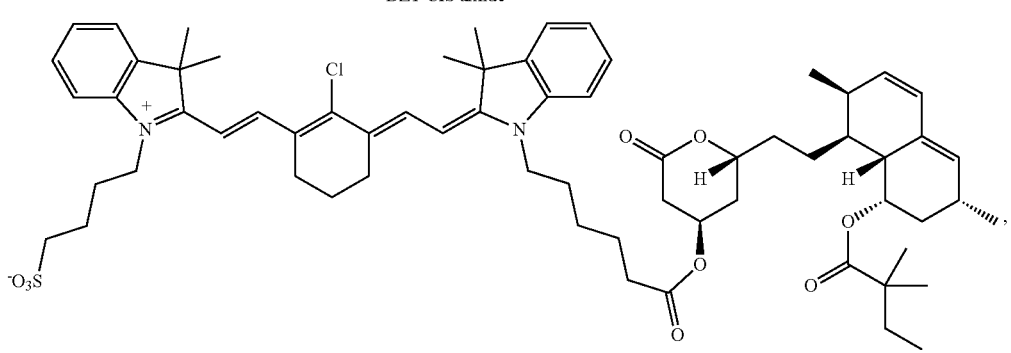

DZ1-SIM ester

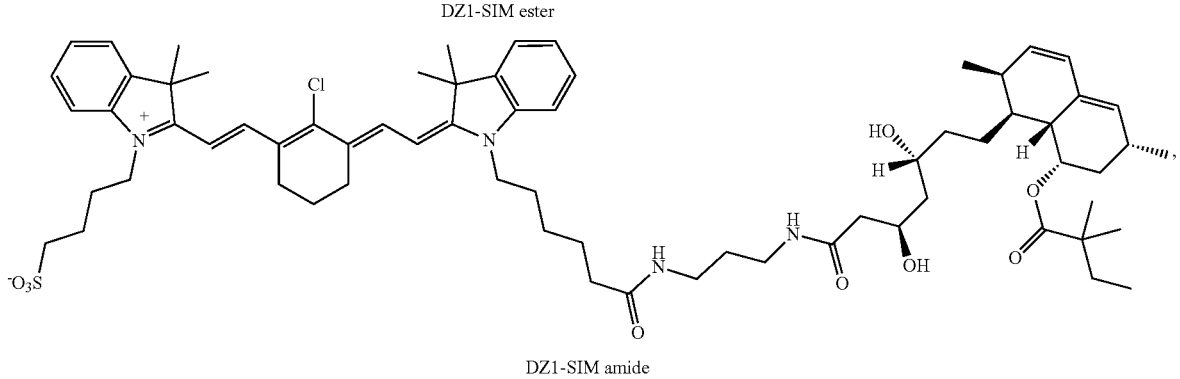

DZ1-SIM amide

-continued

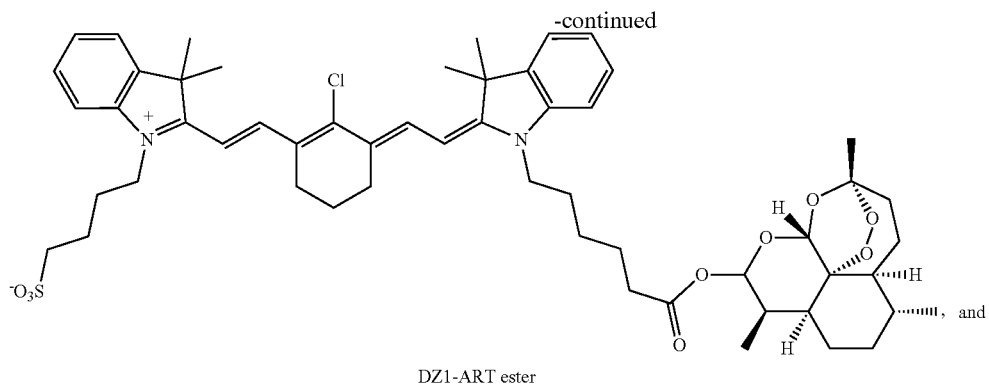

DZ1-ART ester

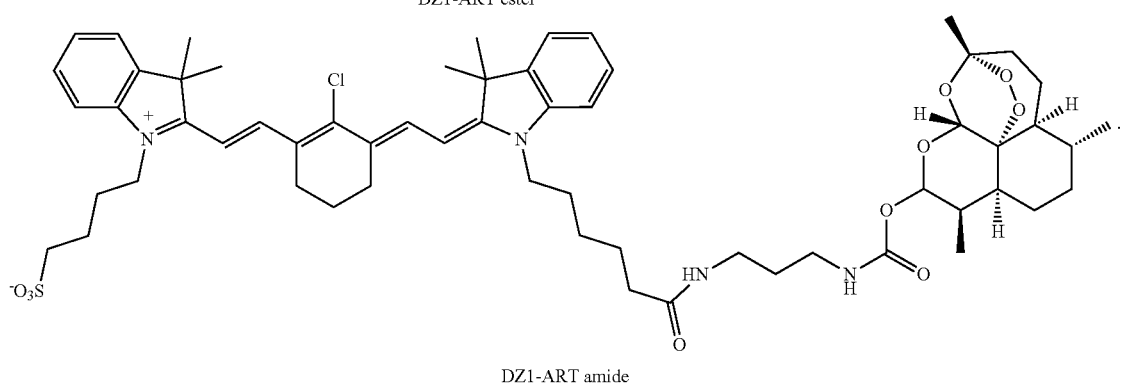

DZ1-ART amide

Alternatively to the SIM residue shown in DZ1-SIM above, alternatively, the residue may be the residue of another statin drug. Alternatively to the CIS residue shown above, which is Cisplatin (also known as cis-diamminedichloridoplatinum (II) or CDDP), the DZ1-CIS sensitizer may alternatively comprise the residue of another platin-based anti-neoplastic drug. These sensitizing compounds of the invention may be collectively referred to herein as "sensitizers", "sensitizer compounds", "sensitizing compounds", or simply "compounds". DZ1-CIS or "CIS-sensitizers" collectively refers to DZ1-CIS ester and amide, DZ1-SIM or "SIM sensitizers" collectively refers to .DZ1-SIM ester and amide, and DZ1-ART or "ART sensitizers" collectively refers to .DZ1-ART ester and amide.

According to an embodiment of the present invention, statin-alternatives to Simvastatin for the statin residue of the sensitizer compounds include, without limitation, residues of atorvastatin, fluvastatin, lovastatin, pitavastatin, pravastatin, and rosuvastatin, linked to a DZ1-amide or DZ1-ester via the amide/ester residue as shown above for DZ1-SIM.

According to an embodiment of the present invention, platinum-based alternatives to cisplatin (CIS) for the platin-based residue of the sensitizer compounds include platinum-based anti-neoplastic agents or chemotherapeuticals, including, without limitation, cisplatin, carboplatin (also known as CBDCA), and dicycloplatin (also known as DCP), oxaliplatin, satraplatin, picoplatin, nedaplatin, triplatin, lobapatin, heptaplatin, and lipoplatin.

According to an embodiment of the present invention, the cancer or precancerous cells to be sensitized may be selected from cells of a cancer associated with tyrosine kinase abnormalities, including hematological cancers and solid tumors. In particular, such cancers include those where the cancer or precancerous cells overexpress a tyrosine kinase, and in particular EGFR. Certain cancers may be associated with mutations that lead to EGFR overexpression (also known as upregulation or overactivity) and these and other cancers that may benefit from EGFR inhibitors include, without limitation, lung cancer, NSCLC, squamous-cell carcinoma of the lung, pancreatic cancer, kidney cancer, breast cancer, metastatic breast cancer, anal cancers, colorectal cancer, renal cell carcinoma, glioblastoma, thyroid cancer, and epithelian tumors of the head and neck. For kidney cancer, sensitizers may be particularly useful in combination with Everolimus (m-TOR inhibitor), to sensitize kidney tumor, cancer or pre-cancerous cells to the growth inhibitory effects of Everolimus.

According to an embodiment of the present invention, to sensitize tumor cells, cancer cells, or pre-cancerous cells to the treatment with a TKI, a patient having a TKI associated cancer may preferably be administered with a sensitizer of the invention prior to or concurrently with TKI administration. Alternatively, for treatment of cancers cells that already developed TKI resistance, the sensitizer may be administered to the patient after one or more initial TKI administration, before or concurrently with one or more further TKI administration.

According to an embodiment of the present invention, the cancer or precancerous cells to be sensitized may be cells that expresses wildtype EGFR, or may be cells that express a mutated variant of EGFR.

According to an embodiment of the present invention, the cancer or precancerous cells to be sensitized may be selected from lung cancer, NSCLC, SCLC, pancreatic cancer, kidney cancer, lymphoma, prostate cancer, colorectal cancer, skin cancer, HCC cancer, and breast cancer, squamous-cell carcinoma of the lung, anal cancers, glioblastoma, and epithelian tumors of the head and neck.

According to an embodiment of the present invention, the cancer or precancerous cells to be sensitized may be a Non-small-cell lung carcinoma selected from a Squamous-cell carcinoma, Adenocarcinoma (Mucinous cystadenocarcinoma), Large-cell lung carcinoma, Rhabdoid carcinoma, Sarcomatoid carcinoma, Carcinoid, Salivary gland-like carcinoma, Adenosquamous carcinoma, Papillary adenocarcinoma, and Giant-cell carcinoma.

According to an embodiment of the present invention, the tumor, cancer or precancerous cells to be sensitized may be a Small-cell lung carcinoma, including a Combined small-cell carcinoma.

According to an embodiment of the present invention, the tumor, cancer or precancerous cells to be sensitized may be a Non-carcinoma of the lung, including a Sarcoma, Lymphoma, Immature teratoma, and Melanoma.

According to an embodiment of the present invention, a pharmaceutical composition comprising one or more sensitizer compound is provided. The pharmaceutical composition may be for human or for veterinary use, and comprise one or more compound of the invention (or a salt, solvate, metabolite, or derivative thereof) with one or more pharmaceutically acceptable carrier and/or one or more excipient and/or one or more active. The one or more carrier, excipient and/or active may be selected for compatibility with the other ingredients of the formulation and not unduly deleterious to the recipient thereof. Such carriers are known in the art and may be selected as will be apparent to a person of ordinary skill in the art.

According to an embodiment of the present invention, routes of administration for the compounds and pharmaceutical compositions include, but are not limited to: oral, intraperitoneal, subcutaneous, intramuscular, transdermal, rectal, vaginal, sublingual, intravenous, buccal, or inhalational. In some embodiments, the pharmaceutical compositions of the invention contain a pharmaceutically acceptable excipient suitable for rendering the compound or mixture administrable via the above routes of administration. Alternatively, the pharmaceutical compositions may be administered through urogenital routes, e.g. via internal organs, topical lesions, or access by instillation (such as urinary bladder, vaginal cannel).

According to an embodiment of the present invention, the active ingredients can be admixed or compounded with a conventional, pharmaceutically acceptable excipient. A mode of administration, vehicle, excipient or carrier should generally be substantially inert with respect to the active agent, as will be understood by those of ordinary skill in the art. Illustrative of such methods, vehicles, excipients, and carriers are those described, for example, in Remington's Pharmaceutical Sciences, 18th ed. (1990), the disclosure of which is incorporated herein by reference. The excipient must be "acceptable" in the sense of being compatible with the other ingredients of the formulation and not deleterious to the recipient thereof.

According to an embodiment of the present invention, the pharmaceutical formulations may be conveniently made available in a unit dosage form by any of the methods generally known in the pharmaceutical arts. Generally speaking, such methods of preparation comprise presenting the formulation in a suitable form for delivery, e.g., forming an aqueous suspension. The dosage form may optionally comprise one or more adjuvant or accessory pharmaceutical ingredient for use in the formulation, such as mixtures, buffers, and solubility enhancers.

According to an embodiment of the present invention, parenteral dosage forms (i.e. that bypass the GI tract) of the pharmaceutical formulations include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

According to an embodiment of the present invention, suitable vehicles that can be used to provide parenteral dosage forms of the compounds of the invention include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound of the invention as disclosed herein can also be incorporated into the parenteral dosage forms of the disclosure, including conventional and controlled-release parenteral dosage forms.

According to an embodiment of the present invention, formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents.

According to an embodiment of the present invention, injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

According to an embodiment of the present invention, compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

According to an embodiment of the present invention, forms suitable for oral or sublingual administration include tablets, troches, capsules, elixirs, suspensions, syrups, wafers, chewing gum, or the like prepared by art recognized procedures. The amount of active compound in such therapeutically useful compositions or preparations is such that a suitable dosage will be obtained. A syrup formulation will generally consist of a suspension or solution of the compound or salt in a liquid carrier, for example, ethanol, glycerine or water, with a flavoring or coloring agent.

According to an embodiment of the present invention, solid dosage forms for oral administration include capsules, tablets, pills, powders, and granules. In such solid dosage forms, the active compound is mixed with at least one inert, and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

According to an embodiment of the present invention, solid compositions of a similar type can also be employed as fillers in soft and hardfilled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

According to an embodiment of the present invention, the active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

According to an embodiment of the present invention, the active compounds be present in form of salts, which may be particularly suitable for use in the treatment of cancer. The salts of the present invention may be administered to the patient in a variety of forms, depending on the route of administration, the salt involved, and the cancer being treated. For example, an aqueous composition or suspension of the salts may be administered by injection, or in the form of a pharmaceutical matrix by injection or surgical implantation, at a desired site. The particular technique employed for administering the matrix may depend, for example, on the shape and dimensions of the involved matrix. In some embodiments, the salt is introduced substantially homogeneously in a tumor to minimize the occurrence in the tumor of cold (untreated) areas. In certain embodiments, the salt is administered in combination with a pharmaceutically acceptable carrier. A wide variety of pharmaceutically acceptable carriers are available and can be combined with the present salts, as will be apparent to one of ordinary skill in the art.

According to an embodiment of the present invention, effective amounts, toxicity, and therapeutic efficacy of the active compounds can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods exhibit large therapeutic indices. A therapeutically effective dose can be estimated initially from cell culture assays. Also, a dose can be formulated in animal models to achieve a circulating plasma concentration range that includes the IC50 (i.e., the concentration of the compound of the invention, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

According to an embodiment of the present invention, the dosage of a pharmaceutical formulation as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule/regimen can vary, e.g. once a week, daily, or in particular predetermined intervals, depending on a number of clinical factors, such as the subject's sensitivity to each of the active compounds.

According to an embodiment of the present invention, a composition comprising one or more sensitizer compound of the invention can be administered to tumor, cancer or pre-cancerous cells of a patient, in an effective dose to sensitize the cells to a TKI and thus treat or inhibit cancer in combination with administration of the TKI. The TKI may be concurrently administered, or may be administered shortly before or shortly after the sensitizer compound, e.g. according to a particular dosing regimen that takes into account e.g. the concentration of the sensitizer and the TKI in the blood, and the half-life of these actives, as will be apparent to a person of ordinary skill.

According to an embodiment of the present invention, an effective dose of a composition comprising a sensitizer compound can be administered to a patient once. Alternatively, an effective dose of a composition comprising a compound of the invention can be administered to a patient repeatedly. In certain embodiments, an effective dose of a composition comprising a compound of the invention can be administered to a patient via skin patches, instillation into urinary bladder through urethral, or vaginal channel through ring implantation. Patients can be administered a therapeutic amount of a composition comprising a compound of the invention. A composition comprising a compound of the invention can be administered over a period of time, such as over a 5 minute, 10 minute, 15 minute, 20 minute, or 25 minute period. If warranted, the administration can be repeated, for example, on a regular basis, such as hourly for 3 hours, 6 hours, 12 hours or longer or such as biweekly (i.e., every two weeks) for one month, two months, three months, four months or longer. In some instances, after an initial treatment regimen, the treatments can be administered on a less frequent basis. For example, after administration biweekly for three months, administration can be repeated once per month, for six months or a year or longer. Administration of a composition comprising one or more sensitizer compound of the invention together with a TKI in a coordinated administration schedule to ensure exposure to both, and preferably concurrent exposure to both, can reduce levels of a biomarker or a symptom of cancer.

According to an embodiment of the present invention, the sensitizer compound may be administered to a subject up to several days, hours or minutes before administration of the TKI. For example, about 20-24 h before, about 15-20 hours before, about 12-15 hours before, about hours before, about 8-10 hours before, about 2-8 hours before, about 1-6 hours before, about 1-4 hours before, about 1-3 hours before, about 1-2 hours before, about 0.5-1.5 hours before, or about 45-min. about 30 minutes, or about 15 minutes before TKI administration.

According to an embodiment of the invention, the concentration of the TKI inhibitor may depend on the typical dosage of the particular TKI formulation, may be adapted to expose the tumor, cancer or pre-cancerous cells to concentrations of, e.g., from about 0.1 to about 100 uM. For example, for Gefitinib, the concentration may be about 0.5 to about 5 uM, and may be combined with about 1 to 10 uM DZ1-SIM amide or ester, or 1 to 10 uM DZ1-CIS amide or ester.

According to an embodiment of the invention, the amount of the actives (sensitizer compound or compounds, and TKI) in the pharmaceutical composition can be based on weight, moles, or volume. In some embodiments, the pharmaceutical composition comprises at least compounds of the invention. In some embodiments, the pharmaceutical composition comprises at least 0.1% compounds of the invention. In some embodiments, the pharmaceutical composition comprises at least 0.5% compounds of the invention. In some embodiments, the pharmaceutical composition comprises at least 1% compounds of the invention. In some embodiments, the pharmaceutical composition comprises at least 2% compounds of the invention. In some embodiments, the pharmaceutical composition comprises at least 3% compounds of the invention. In some embodiments, the pharmaceutical composition comprises at least 4% compounds of the invention. In some embodiments, the pharmaceutical composition comprises at least 5% compounds of the invention. In some embodiments, the pharmaceutical composition comprises at least 10% compounds of the invention. In some embodiments, the pharmaceutical composition comprises 0.01%-99% of the compounds of the invention. In some embodiments, the pharmaceutical composition comprises 0.05%-90% of the compounds of the invention. In some embodiments, the pharmaceutical composition comprises 0.1%-85% of the compounds of the invention. In some embodiments, the pharmaceutical composition comprises of the compounds of the invention. In some embodiments, the pharmaceutical composition comprises 1%-75% of the compounds of the invention. In some embodiments, the pharmaceutical composition comprises 2%-70% of the compounds of the invention. In some embodiments, the pharmaceutical composition comprises 3%-65% of the compounds of the invention. In some embodiments, the pharmaceutical composition comprises 4%-60% of the compounds of the invention. In some embodiments, the pharmaceutical composition comprises 5%-50% of the compounds of the invention.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound of the invention.

Various embodiments provide for a bifunctional method of cell sensitization to TKIs, cancer therapy and imaging, wherein in addition to sensitization, pre-cancerous or cancerous cells and tumors in a patient in need thereof are identified, imaged and/or localized. The method can comprise providing one or more DZ1-dye-residue comprising sensitizer compound; administering the one or more sensitizer compound to a patient who is further administered with one or more TKI; and performing optical imaging. This allows to visually follow and control stop of tumor growth and/or shrinkage, e.g. to confirm or personalize an optimized dosage, and/or determine the location of tumor(s) and/or metastase(s) within the NIR spectral region of DZ1. In various embodiments, imaging may be performed, for example, about 6 to 48 hours post injection. Imaging may be performed in comparison to normal tissue/cells.

Various embodiments provide for a bifunctional method of conducting in situ pharmacokinetic and pharmacodynamic analyses of the sensitizer compounds of the present invention and its drug payload in a tumor or normal cell or tissue. The method can comprise providing the sensitizer; contacting it with the cancer cells, tumor, or normal cell or tissue; and imaging the cancer cells, tumor, or normal cell or tissue, followed by pharmacokinetic and/or pharmacodynamics analyses, e.g. determining the fluorescence (or changes thereof) over time.

DETAILED DESCRIPTION OF THE DRAWINGS

FIG. 1 illustrates IC50 results for human lung cancer cell lines tested in Example 1 with DZ1-SIM ester and amide, respectively, compared to Simvastatin. The results show that Simvastatin is equally or more effective than DZ1-SIM ester or DZ1-SIM amide and that DZ1-SIM ester is more effective than DZ1-SIM amide.

Figures 1, 1A, 2:
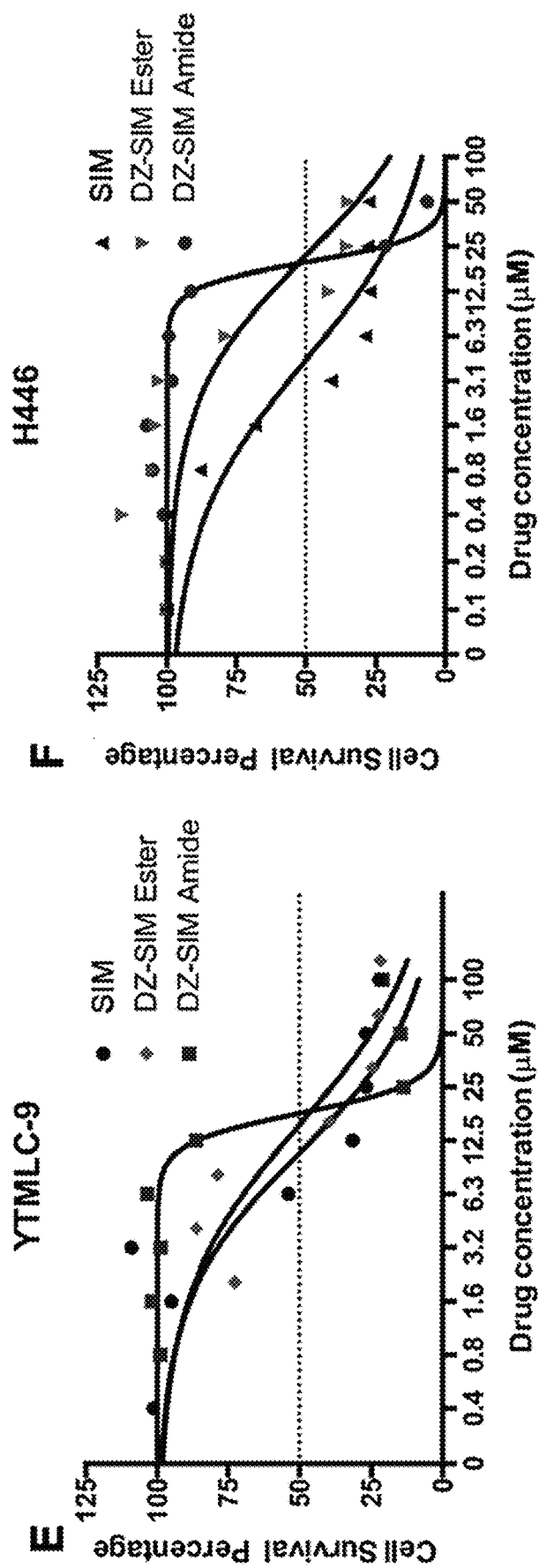

FIG. 2 illustrates IC50 results for NSCLC cell lines tested in Example 2 with DZ1-SIM ester and amide, respectively, showing sensitization of EGFR-mutated cells to TKIs. The results show that DZ1-SIM amide is useful for sensitizing both resistant and non-resistant EGFR mutated cancer cells to TKIs, and that DZ1-SIM allows to overcome TKI resistance and/or reduce TKI dosage.

Figure 3:
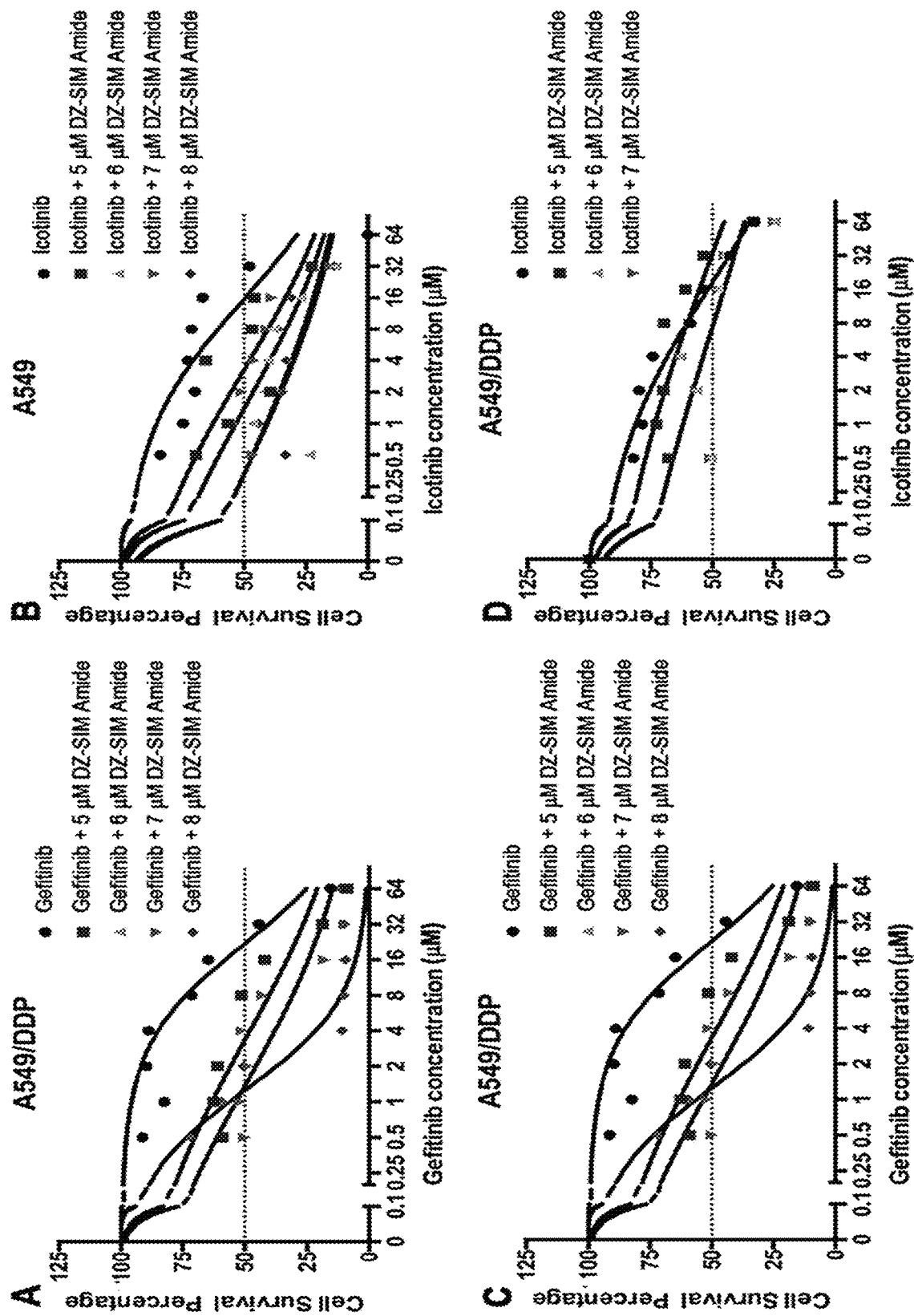
FIG. 3A illustrates the calculated 50% inhibitory concentration (IC50) of DZ1-SIM Amide with various concentrations of Tyrosine Kinase Inhibitor drug, Gefitinib, as tested in cell line A549/DDP.
FIG. 3B illustrates the calculated 50% inhibitory concentration (IC50) of DZ1-SIM Amide with various concentrations of Tyrosine Kinase Inhibitor drug, Icotinib, as tested in cell line A549.
FIG. 3C illustrates the calculated 50% inhibitory concentration (IC50) of DZ1-SIM Amide with various concentrations of Tyrosine Kinase Inhibitor drug, Gefitinib, as tested in cell line A549/DDP.
FIG. 3D illustrates the calculated 50% inhibitory concentration (IC50) of DZ1-SIM Amide with various concentrations of Tyrosine Kinase Inhibitor drug, Icotinib, as tested in cell line A549/DDP.

FIG. 3 illustrates IC50 results for NSCLC cell lines tested in Example 3 with DZ1-SIM amide, showing sensitization of EGFR-wild-type cells to TKIs. The results show that in resistant and non-resistant cells, the dose of TKIs can be reduced while retaining the TKI's effects, and consistently effective TKI sensitization also in cancer cells without EGFR mutations.

Figure 4:
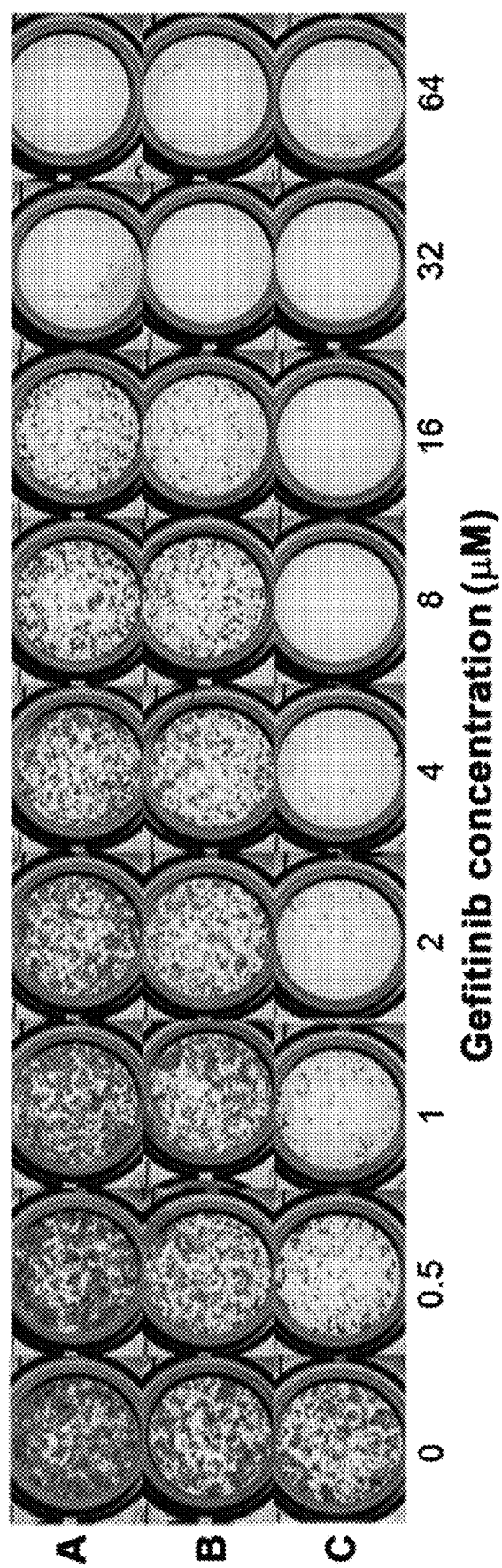
FIG. 4 illustrates crystal violet assay results for a lung carcinoma cell line tested in Example 4 with DZ1-SIM amide, showing sensitization of cells to TKIs by DZ1-SIM amide.

FIG. 4 illustrates crystal violet assay results for a lung carcinoma cell line tested in Example 4 with DZ1-SIM amide. The results show sensitization of cells to TKIs by the sensitizer in concentration-dependent manner, and an increase effectiveness of Gefitinib to excellent TKI effects at concentrations as low as about 0.5 uM (with the sensitizer at about 5 uM).

Figure 5:
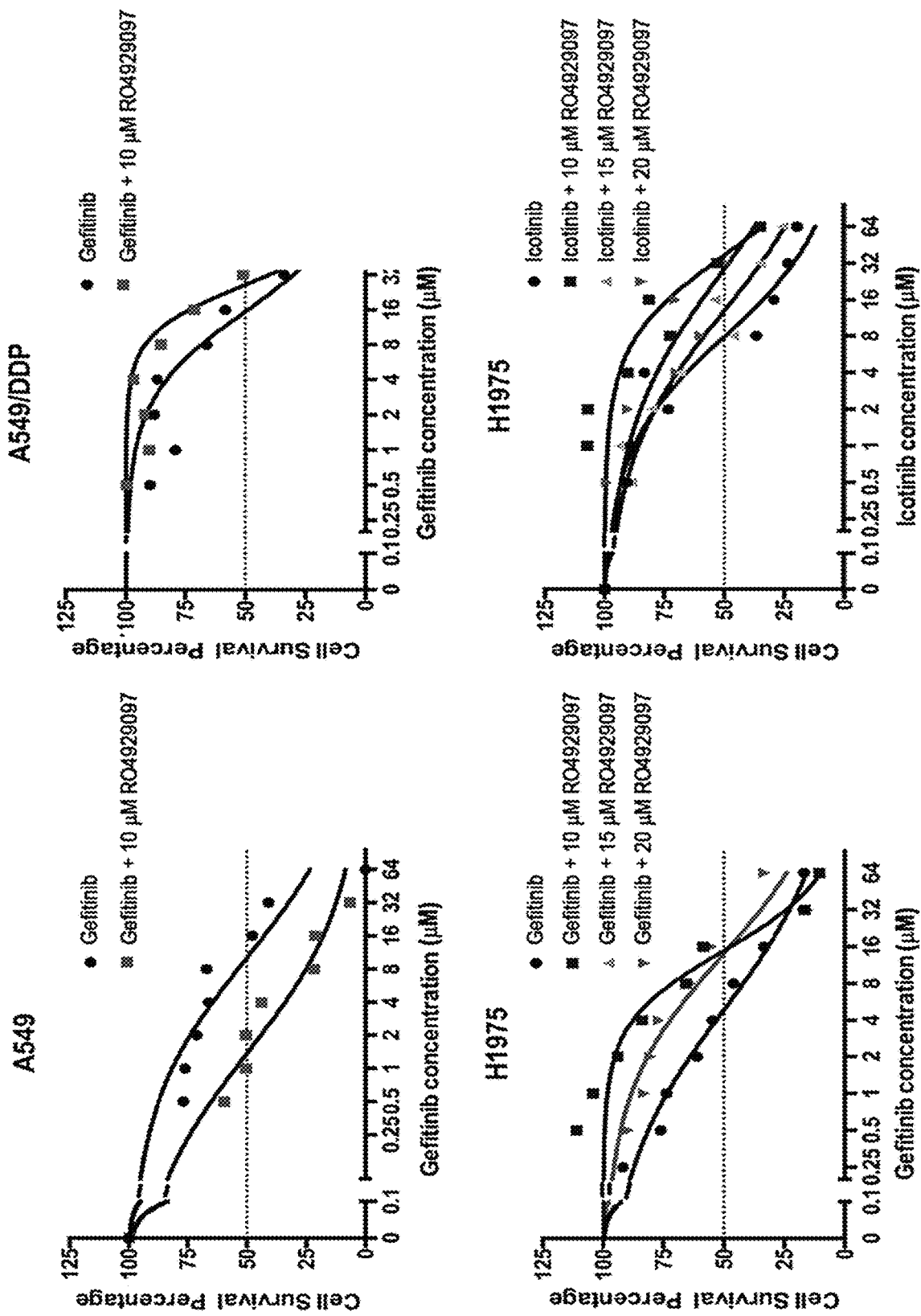
FIG. 5 (Top Left) illustrates the calculated 50% inhibitory concentration (IC50) of Tyrosine Kinase Inhibitor drug, Gefitinib, with various concentrations of Gamma-secretase inhibitor RO492909, as tested in cell line A549.

FIG. 5 illustrates IC50 results lung cancer cells tested in Example 5 with gamma-secretase inhibitor-RO4929097. The results show that RO4929097 does not consistently sensitize the cells to TKI with lack of concentration-dependency and lack of sensitization in cells of EGFR wild-type; only A549 responded successfully to sensitization, while A549/DDP, H-1975 and H-1650 did not consistently respond.

EXEMPLARY EMBODIMENTS

The materials and methods used in the following embodiments were as follows. Simvastatin was purchased from Ark Pharm, Inc. (Arlington Heights, IL). Cisplatin was purchased from MedKoo Biosciences, Inc. (Chapel Hill, NC). All other chemicals and reagents were purchased from standard sources such as Sigma-Aldrich and/or VWR and were of highest quality available. Deionized water (18.2Ω) used for making solutions was obtained from Milli-Q Direct Ultrapure Water System from Millipore (Billerica, MA, USA). All intermediates were characterized by 1H NMR and mass analysis and the purity of compounds were analyzed by HPLC. 1H NMR data were collected on Bruker 400 MHz spectrometers using standard parameters; chemical shifts are reported in ppm (δ) in reference to residual non-deuterated solvent. ESI mass spectroscopy analysis was performed on new compounds at Mass Spectrometry and Biomarker Discovery Core facility using a Thermo Fisher LTQ Orbitrap Elite system.

DZ1 may be synthesized as follows, using deionised Ultrapure water (resistivity, 18.2 MΩcm) and High-performance liquid chromatography (HPLC) grade solvents. Analytical reversed-phase (RP) high-performance liquid chromatography (HPLC) is performed on an Agilent system with a 1260 Infinity Diode-Array Detector with an Apollo C18 RP column (5 μm, 150×4.6 mm). The mobile phase changes from 50% solvent A (0.1% trifluoroacetic acid in 80% water) and 50% solvent B (0.1% trifluoroacetic acid in 80% aqueous acetonitrile) to 100% solvent B over a period of 30 min at a flow rate of 1 mL/min (monitoring at 254 and 780 nm). ESI-time-of-flight mass spectroscopy (ESI-TOF-MS) analysis is performed on a LCT Premier Mass Spectrometer. 1HNMR spectra are recorded on a Bruker 400 MHz NMR spectrometer.

A reaction scheme for DZ synthesis is shown below.

Scheme 1.

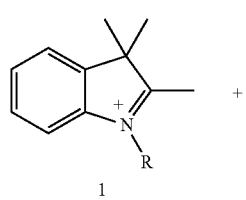

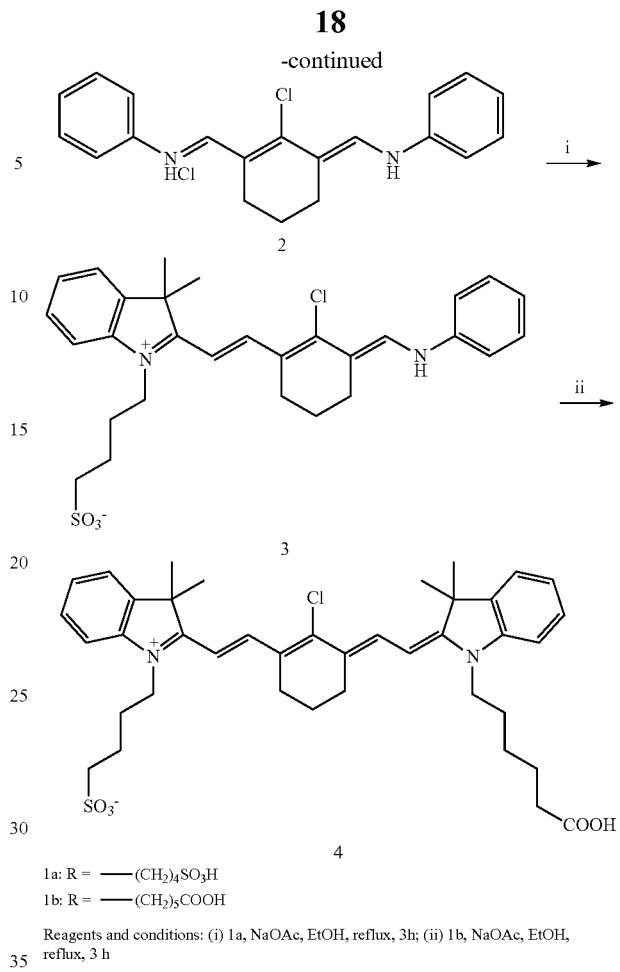

1a: R = —(CH$_2$)$_4$SO$_3$H
1b: R = —(CH$_2$)$_5$COOH

Reagents and conditions: (i) 1a, NaOAc, EtOH, reflux, 3h; (ii) 1b, NaOAc, EtOH, reflux, 3 h Synthesis of compound 3: To the mixture of 1a (2.0 g, 6.78 mmol) and Vilsmeier-Haack reagent 2 (3.0 g, 8.36 mmol) in EtOH (50 ml) is added CH$_3$COONa (0.56 g, 6.78 mmol), the resulted mixture is heated to reflux for 3 h. The reaction mixture is poured into 200 ml of ice-water. The precipitate is collected and recrystallized from ethanol-acetone to afford desired product 3 as a dark blue solid (2.1 g, yield 56%). $^1$H NMR (DMSO-d6, 400 MHz) δ 10.20 (s, 1H), 8.43 (d, 1H, J=16 Hz), 8.19 (s, 1H), 7.71 (m, 2H), 7.53-7.39 (m, 6H), 7.16 (m, 1H), 6.62 (d, 1H, J=12 Hz), 4.38 (m, 2H), 2.71 (m, 4H), 2.52 (m, 2H), 1.87 (m, 4H), 1.75 (m, 2H), 1.69 (s, 6H). MS (ESI-TOF) C$_{29}$H$_{34}$ClN$_2$O$_3$S [M+H]$^+$: 525.1979.

Synthesis of DZ dye 4: To the mixture of 1b (0.5 g, 1.4 mmol) and compound 3 (1 g, 1.9 mmol) in EtOH (20 ml) is added CH$_3$COONa (128 mg, 1.5 mmol), the resulting solution is heated to reflux for 3 h. The reaction mixture is poured into 100 ml of water. The solid is collected and crystallized from methanol-water to afford desired product 4 as a dark green solid (0.8 g, yield 73%). $^1$H NMR (DMSO-d6, 400 MHz) δ 11.99 (s, 1H), 8.26 (m, 2H), 7.61-7.22 (m, 8H), 6.43 (d, 1H, J=16 Hz), 6.23 (d, 1H, J=16 Hz), 4.23 (m, 4H), 2.72 (m, 4H), 2.21 (m, 2H), 1.86 (m, 4H), 1.73 (m, 6H), 1.67 (s, 6H), 1.66 (s, 6H), 1.57 (m, 2H), 1.40 (m, 2H). MS (ESI-TOF) C$_{40}$H$_{50}$ClN$_2$O$_5$S [M+H]$^+$: 705.3152. HPLC retention time: 17.375 min.

For tests of cells and cell lines, unless otherwise specified, the cells were cultured in medium containing 10% FBS grown as monolayers and treated with different concentrations of sensitizer compounds and/or TKI for 72 h. IC50s (defined as the concentration that resulted in a 50% decrease of cell proliferation as assessed by a Crystal Violet Assay) were determined in these cultured cells. Data represents the mean±Standard Error of the Mean (SEM) from at least three independent experiments.

For the crystal violet assay, a 96-well assay was used which is based on the uptake and elution of crystal violet dye by the cells in each well. Falcon 96-well plates were used, and cells were plated per well (in T medium containing 1% charcoal stripped CS and 2% TCM). 24 hours later, the cells were downshifted to serum-free condition with various concentrations of test drugs. To avoid stripping poorly adherent cells with each media change, media was partially removed by gentle suction and 100 µl of fresh media was added in 50 µl aliquots. The medium was changed every 2 days; 7-10 days later the cells were fixed in 1% glutaraldehyde (Sigma) and stained with 0.5% crystal violet (Sigma). Plates were washed and air dried, and the dye was eluted with 100 µl Sorensen's solution (9 mg trisodium citrate in 305 ml distilled H2O, 195 ml of HCl, and 500 ml 90% ethanol). Absorbance of each well was measured by a Titertek Multiskan TCC/340 (Flow Laboratories, McLean, VA) at 560 nm. Control experiments demonstrated that absorbance is directly proportional to the number of cells in each well.

Example 1

Human lung cancer cell lines used include non-small cell lung cancer (NSCLC) cell lines and small cell lung cancer cell lines (SCLC). The NSCLC cell lines include parental A-549, A-549/DDP (a cisplatin-resistant cell line), 95D (a metastatic variant of the parental non-metastatic a squamous YTMLC line. H446 is a SCLC cell line. Cells were cultured in medium containing 10% FBS grown as monolayers and treated with different concentrations of drugs for 72 h. IC50s (defined as the concentration that resulted in a 50% decrease of cell proliferation as assessed by a Crystal Violet Assay) were determined in these cultured cells. Data represents the mean±Standard Error of the Mean (SEM) from at least three independent experiments. Drugs tested and compared were Simvastatin, DZ1-Simvastatin ester (DZ1-SIM E), DZ1-Simvastatin amide (DZ1-SIM A), Cisplatin (CIS), and DZ1-CIS. The drugs were used as single agents.

Figures 1, 1B:
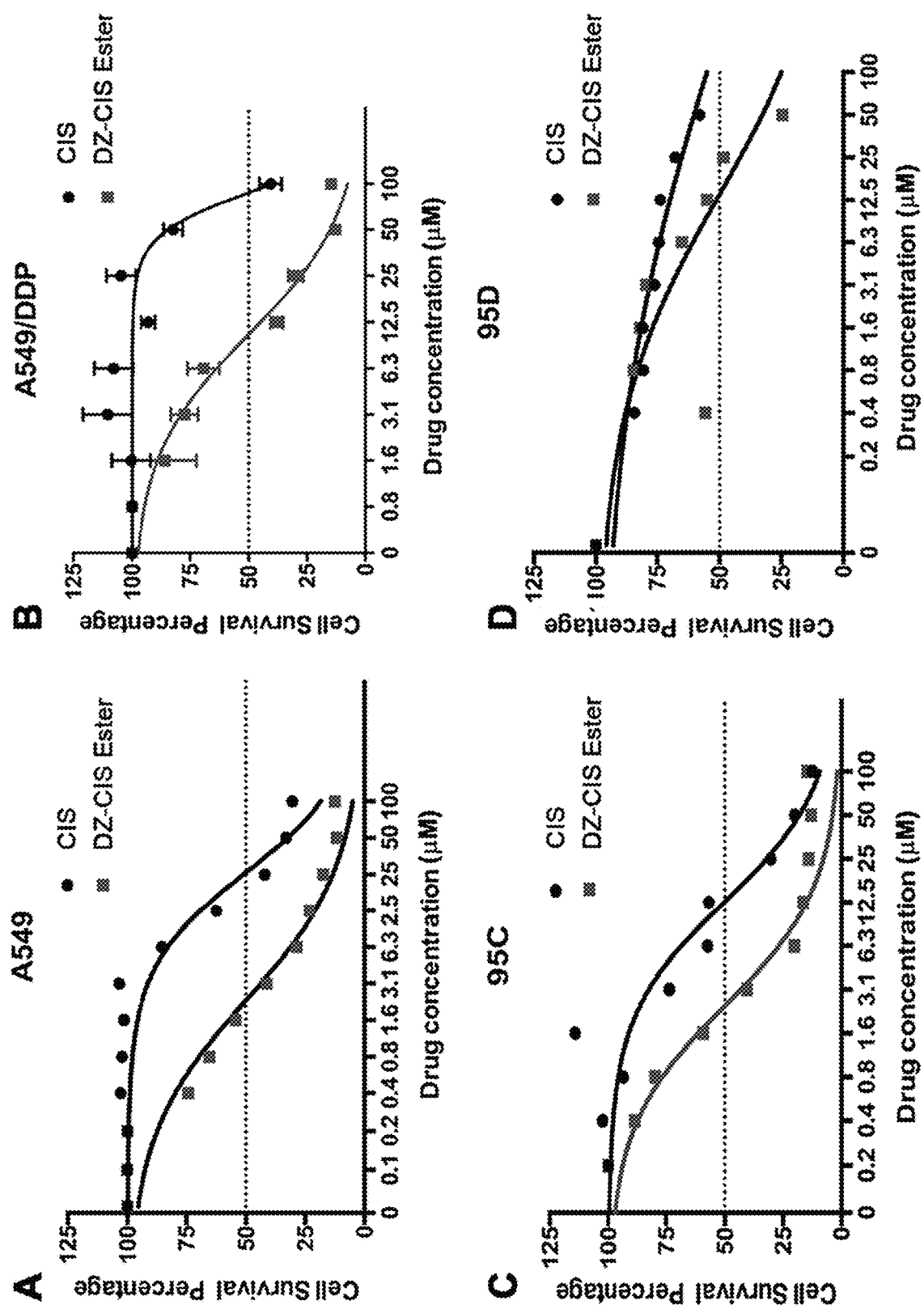
Figure 2:
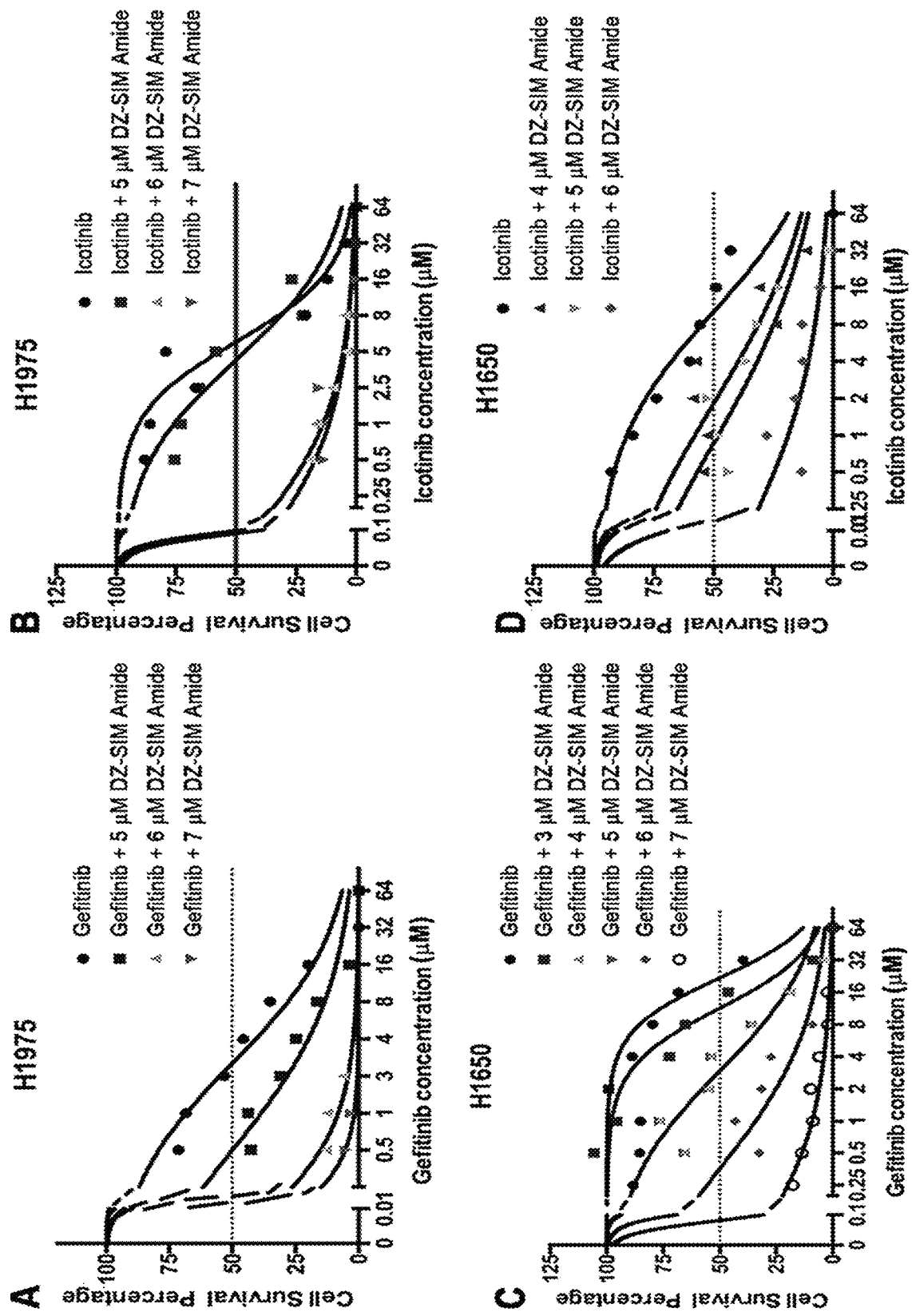

As shown in the table below, the results indicate that Simvastatin is equal effective or more effective than DZ1-SIM ester or DZ1-SIM amide and that DZ1-SIM ester is more effective than DZ1-SIM amide in all of the lung cancer cell lines tested in vitro. DZ-CIS Ester derivative is consistently more effective than CIS in all of the human lung cancer cell lines tested Panel A-F of FIG. 1A shows the calculated 50% inhibitory concentration (IC50) on a logarithmic scale for the cell lines tested in Example 1 with DZ1-SIM ester and amide, respectively; Panel A-F of FIG. 1B shows the same for CIS and DZ1-CIS. The data is expressed as means+/−SEM from two assays done in quadruplicate. The viability of control cells treated with dimethyl sulfoxide was assigned a value of 100. The combined numeric results of these assays are presented in Table 1 above.

Example 2

Example 2 shows combination results with EGFR Tyrosine Kinase Inhibitor drugs (TKIs) in an in vitro model of human lung cancer, EGFR-mutated NSCLC cell lines H1975 and H1650, in the presence or absence of sensitization by DZ1-SIM amide in different concentrations. Human lung cell lines H1975 and H1650 serve as models for lung cancer cells with EGFR mutations. The example is performed as indicated in Example 1, with changes in cell lines used, and in drugs and their concentrations used, as indicated below. H-1975 and H-1650 were cultured in medium containing 10% FBS and treated with various concentrations of a TKI (Gefitinib or Icotinib), in the presence or absence of varying concentrations of sensitizing DZ1-SIM amide (in concentrations from 3-7 uM) for 72 h. IC50s (defined as the concentration that resulted in a 50% decrease of cell proliferation as assessed by a Crystal Violet Assay) were determined in these cultured cells. Data represent the mean from at least three independent experiments. In FIG. 2, panels A-D show the results from two assays performed in quadruplicate as described above. The viability of control cells treated with dimethyl sulfoxide was assigned a value of 100.

The IC50 results in the table below and in FIG. 2 (see panels A-D) compare DZ1-SIM amide sensitized and non-sensitized cells, and show that DZ1-SIM amide sensitizes the cancer cells to the EGFR-mediated antitumor effect and cytotoxicity of TKIs (shown here for Gefitinib and Icotinib). In comparison to the TKI alone, their combination with the DZ1-SIM amide greatly reduced the IC50 of these cells towards Gefitinib or Icotinib, respectively. This shows that the DZ1-SIM amide can be used to sensitize TKI-resistant EGFR mutated cancer cells to the antitumor effects of TKIs, and that in resistant and non-resistant cells, in presence of DZ1-SIM, the dose of TKIs can be greatly reduced while retaining a sufficient antitumor effect.

| | IC50 | | | | | |
|---|---|---|---|---|---|---|
| | NSCLC | | | | | |
| Drugs | A549 parental | A549/DDP (Cisplatin Resistant) | 95D (Met) | 95C (Non-Met) | YTMLC | SCLC H446 |
| SIM | 4.2 ± 1.2 | 5.3 ± 1.1 | 1.7 ± 1 | 2 ± 1.2 | 10.6 ± 1 | 4.3 ± 1.3 |
| DZ1-SIM E | 4 ± 1.1 | 3.6 ± 1.1 | 6.6 ± 1 | 2.4 ± 1 | 11.7 ± 1.3 | 23.4 ± 1.3 |
| DZ1-SIM A | 8 ± 1 | 8 ± 1 | 10.2 ± 1 | 7.7 ± 1.3 | 17.8 ± 1.1 | 19.2 ± 1 |
| CIS | 26.0 ± 1.2 | 90.0 ± 1.0 | >100.0 ± 1.1 | 12.7 ± 1.0 | 16.2 ± 1.0 | 107.3 ± 1.0 |
| DZ1-CIS | 1.8 ± 1.0 | 10.2 ± 1.2 | 13.7 ± 1.3 | 2.4 ± 1.1 | 2.2 ± 1.0 | 23.4 ± 1.0 |

| | H1975 Mean (95% CI) | H1650 Mean (95% CI) |
|---|---|---|
| DZ1-SIM Amide | 5.5 (4-6) | 6.2 (4.7-8.3) |
| Gefitinib | 2.5 (2.1-3.1) | 22 (17-28) |
| Gefitinib + 3 uM DZ1-SIM Amide | — | 11.4 (9-14) |
| Gefitinib + 4 uM DZ1-SIM Amide | — | 3 (2-4.4) |
| Gefitinib + 5 uM DZ1-SIM Amide | 0.5 (0.3-0.7) | 3 (2-4.4) |
| Gefitinib + 6 uM DZ1-SIM Amide | 0.1 (0.02-0.4) | 0.4 (0.2-0.8) |
| Gefitinib + 7 uM DZ1-SIM Amide | 0.1 (0.01-1.4) | 0.01 (0.003-0.7) |
| Icotinib | 4.8 (3.5-6.6) | 10.2 (6.6-15.7) |
| Icotinib + 4 uM DZ1-SIM Amide | — | 1.8 (1-3.2) |
| Icotinib + 5 uM DZ1-SIM Amide | 3.4 (2.4-4.9) | 0.9 (0.4-1.7) |
| Icotinib + 6 uM DZ1-SIM Amide | 0.1 (0.03-0.2) | 0.02 (0.005-0.6) |
| Icotinib + 7 uM DZ1-SIM Amide | 0.04 (0.003-0.4) | — |

Example 3

Example 3 shows combination results with EGFR Tyrosine Kinase Inhibitor drugs (TKIs) in an in vitro model of human lung cancer, EGFR-wild-type NSCLC cell lines A549 and A549/DDP, in the presence or absence of sensitization by DZ1-SIM Amide in different concentrations. Human lung cell lines A549 and A549/DDP serve as models for lung cancer cells without EGFR mutations; their sensitization of TKIs-induced growth inhibition is shown. EGFR-wild type human lung cancer cell lines, A549/DDP and A549, were cultured in medium containing 10% FBS and treated with various concentrations of TKIs (Gefitinib or Icotinib), in the presence or absence of DZ1-SIM amide in concentrations from 5-9.5 uM for 72 h. IC50s (defined as the concentration that resulted in a 50% decrease of cell proliferation as assessed by a Crystal Violet Assay) were determined in these cultured cells. Data represent the mean from at least three independent experiments. The data in FIG. 3 is expressed as means+/−SEM from two assays done in quadruplicate. The viability of control cells treated with dimethyl sulfoxide was assigned a value of 100. The table below and FIG. 3 shows that in comparison to the TKIs alone, DZ1-SIM amide greatly reduced the IC50 of TKI-resistant and non-resistant lung cancer cells without EGFR mutations towards TKIs as shown with Gefitinib or Icotinib in a concentration-dependent manner. This shows that the DZ1-SIM amide can be used to sensitize wild-type EGFR lung cancer cells to the antitumor effects of TKIs, and that in resistant and non-resistant cells, in presence of DZ1-SIM amide, the dose of TKIs can be greatly reduced while retaining a sufficient antitumor effect. The results are in agreement with clinical observations in lung cancer patients (detailed results not shown), where it was shown that human lung cancer cell lines with EGFR mutations (IC50s=4.8-10.2 uM) are more sensitive to TKIs than those of human lung cancer cell lines with wild-type EGFR (IC50s=10.2-22 uM). The results show effectiveness in cancer cells both with and without EGFR mutations.

| | A549 | A549/DDP |
|---|---|---|
| | IC50 of TKIs | |
| Gefitinib | 10.2 (6.7-15.5) | 22 (15.5-31) |
| Gefitinib + 5 uM DZ1-SIM Amide | — | 3.3 (2.1-5.3) |
| Gefitinib + 6 uM DZ1-SIM Amide | — | 3.3 (2.1-5.3) |
| Gefitinib + 7 uM DZ1-SIM Amide | 2.8 (1.8-4.3) | 1.3 (0.8-2.2) |
| Gefitinib + 8 uM DZ1-SIM Amide | 1.3 (1-1.6) | 1.2 (1-1.6) |
| Gefitinib + 8.5 uM DZ1-SIM Amide | 0.8 (0.5-1.3) | |
| Gefitinib + 9 uM DZ1-SIM Amide | 0.7 (0.4-1) | |
| Gefitinib + 9.5 uM DZ1-SIM Amide | 0.4 (0.3-0.6) | |
| Icotinib | 15.6 (8.2-30) | 18.6 (13.2-26) |
| Icotinib + 5 uM DZ1-SIM Amide | — | 34.6 (15.4-77) |
| Icotinib + 6 uM DZ1-SIM Amide | — | 7 (2.5-19) |
| Icotinib + 7 uM DZ1-SIM Amide | 3.3 (1.5-6.9) | 7 (2.5-19) |
| Icotinib + 8 uM DZ1-SIM Amide | 0.2 (0.01-2.7) | — |
| Icotinib + 8.5 uM DZ1-SIM Amide | 1.4 (0.6-3) | |
| Icotinib + 9 uM DZ1-SIM Amide | 0.2 (0.05-1) | |

Example 4

A Crystal Violet Staining of a human lung carcinoma cell line (H-1975, a cell line with EGFR mutations), is performed, exposing the cells to various concentrations of Gefitinib alone, in comparison to combined exposure with DZ1-Simvastatin amide. As shown in FIG. 4, Gefitinib is used in concentrations of 64, 32, 16, 8, 4, 2, 1, 0.5 and 0 uM (columns 1-6, row A), the same concentrations of Gefitinib are combined with DZ-Simvastatin Amide in a concentration of 5 uM (row B) and 6 uM (row C). The results show a dramatic increase and synergism of the cytotoxic effects of the TKI Gefitinib by combination with DZ1-Simvastatin amide in a concentration-dependent manner, see e.g. effect of 0.5 uM Gefitinib combined with 6 uM DZ1-SIM Amide.

Example 5

Example 5 shows lack of sensitization with Gamma-secretase inhibitor RO4929097 in EGFR-mutated H1975 only. RO4929097 is combined with EGFR TKIs (Gefitinib or Icotinib) in vitro models of human lung cancer (EGFR-mutated H1975, H-1650 (data not shown), and EGFR-wildtype A549 and A549/DDP lung cancer cell lines). All cells were cultured in medium containing 10% FBS and treated with various concentrations of TKIs (Gefitinib or Icotinib), in the presence or absence of gamma-secretase inhibitor-RO4929097 (in concentrations from 10-20 uM) for 72 h. IC50s (defined as the concentration that resulted in a 50% decrease of cell proliferation as assessed by a Crystal Violet Assay) were determined in these cultured cells. Data in the table represents the mean from at least three independent experiments. Data in the figures is expressed as means+/−SEM from two assays done in quadruplicate, and the viability of control cells treated with dimethyl sulfoxide was assigned a value of 100. The results in the table below and in FIG. 5 show that RO4929097 does not consistently sensitize the cells to TKI-induced antitumor effects, both in EGFR mutated and in EGFR wild-type human lung cancer cell lines.

The results show that sensitization of cells to a TKIs-induced growth inhibition effect by RO4929097 is variable, in particular, RO4929097 enhances Gefitnib in A549 cells but not in H1975 cells or in A549/DDP cells, and shows no consistent concentration-dependent sensitization unrelated to EGFR mutations. As shown by the Crystal Violet assay shown in FIG. 5, RO4929097 (RO) did not consistently decrease the IC50 of TKIs on both EGFR mutated and wild type NSCLC cell lines. Only A549 treated with Gefitinib responded after successful sensitization by RO4929097, while A549/DDP, H-1975 and H-1650 (data not shown) did not respond consistently to either Gefitinib and Icotinib.

|  | H1975 | A549 | A549/DDP |
|---|---|---|---|
| Gefitinib | 5 (4.1-5.8) | 14 (9.5-21) | 15.5 (10.5-22.7) |
| Gefitinib + 10 uM RO | 14.8 (12.6-17.5) | 1.8 (1.4-2.3) | 26.2 (22.2-31) |
| Gefitinib + 15 uM RO | 14.8 (12.6-17.5) | 1 (0.5-2) | 34.5 (30.4-39.1) |
| Gefitinib + 20 uM RO | 14 (7.6-26) | 0.5 (0.2-0.8) | 25.4 (17.5-36.9) |
| Icotinib | 8 (5.7-11) | — | — |
| Icotinib + 10 uM RO | 37.3 (25.7-54) | — | — |
| Icotinib + 15 uM RO | 13 (9.2-18.7) | — | — |
| Icotinib + 20 uM RO | 28.8 (21.3-39) | — | — |

Example 6

Chemical synthesis of DZ1-conjugates for tumor targeting studies may be performed as described below. Simvastatin was purchased from Ark Pharm, Inc. (Arlington Heights, IL). DZ1 (1) is synthesized as described herein above. Cisplatin was purchased from MedKoo Biosciences, Inc. (Chapel Hill, NC). All other chemicals and reagents used for the synthetic processes were purchased from standard sources such as Sigma-Aldrich and/or VWR and were of highest quality available. Deionized water (18.2Ω) used for making solutions was obtained from Milli-Q Direct Ultrapure Water System from Millipore (Billerica, MA, USA). ESI mass spectroscopy analysis was performed on new compounds at Mass Spectrometry and Biomarker Discovery Core facility using a Thermo Fisher LTQ Orbitrap Elite system.

A reaction scheme for the synthesis of the DZ1-simvastatin ester (3) is shown in example 8. DZ1 1 (407 mg, 0.58 mmol), simvastatin 2 (387 mg, 0.92 mmol), 1-ethyl-3-(3-dimethyllaminopropyl) carbodiie hydrochloride (172 mg, 0.89) and DMAP (65 mg, 0.53 mmol) were mixed and dissolved in anhydrous methylene chloride (15 ml). The resulted mixture was stirred for 18 h. The reaction mixture was concentrated on a rotary evaporator. The residue was dissolved in 5 ml of methanol and purified by C18-RP silica chromatography elution with methanol-water to afford desired product 3 as a dark green solid (269 mg, yield 42%). Mass spectrum (ESI) 1105.58 [M+H]+.

Example 7

A reaction scheme for the synthesis of the DZ1-simvastatin amide is shown in example 8. The synthesis of DZ1-simvastatin amide may be performed as follows. To a solution of simvastatin (1 g, 2.39 mmol, 1 eq.) in acetonitrile, propane-1,3-diamine (1 ml, 11.95 mmol, 5 eq.) was added. The mixture was refluxed with continuous stirring for 4 h. The solvent was removed under reduced pressure and the product was dried in high vacuum. The resulting product 5 was used without further purification. The mixture of DZ1 1 (500 mg, 0.71 mmol) 1-ethyl-3-(3-dimethyllaminopropyl) carbodiie hydrochloride (204 mg, 1.07 mmol) and 1-hydroxy-7-azabenzotriazole (115 mg, 0.85 mmol) were dissolved in 10.0 mL CH2Cl2 solution. The mixture was stirred for 15 min, then compound 5 (350 mg, 0.71 mmol) was added and stirred for additional 2 hours at rt. The solvent was removed under reduced pressure and the product was purified by C18-RP silica chromatography elution with methanol-water to afford desired product 6 as a dark green solid 327 mg (39%). Mass spectrum (ESI) 1179.65 [M+H]+.

Example 8

In the example, the chemical synthesis of DZ-conjugates is shown. Simvastatin is purchased from Ark Pharm, Inc. (Arlington Heights, IL). Cisplatin is purchased from MedKoo Biosciences, Inc. (Chapel Hill, NC). DZ (1) is synthesized as described above. All other chemicals and reagents used for the synthetic processes were purchased from standard sources such as Sigma-Aldrich and/or VWR and were of highest quality available. Deionized water (18.2Ω) used for making solutions was obtained from Milli-Q Direct Ultrapure Water System from Millipore (Billerica, MA, USA). ESI mass spectroscopy analysis was performed on new compounds at Mass Spectrometry and Biomarker Discovery Core facility using a Thermo Fisher LTQ Orbitrap Elite system.

DZ-1-SIM ester may be synthesized as illustrated in reaction scheme 2 below, e.g. as follows: DZ-1 (4) (407 mg, 0.58 mmol), simvastatin (5) (387 mg, 0.92 mmol), 1-ethyl-3-(3-dimethyllaminopropyl) carbodiie hydrochloride (172 mg, 0.89) and DMAP (65 mg, 0.53 mmol) were mixed and dissolved in anhydrous methylene chloride (15 ml). The resulted mixture was stirred for 18 h. The reaction mixture was concentrated on a rotary evaporator. The residue was dissolved in 5 ml of methanol and purified by C18-RP silica chromatography elution with methanol-water to afford desired product 6 as a dark green solid (269 mg, yield 42%). Mass spectrum (ESI) 1105.58 [M+H]+.

1H NMR (DMSO-d6, 400 MHz) δ 8.23 (m, 2H), 7.61-7.56 (m, 2H), 7.47 (d, 1H), 7.42-7.36 (m, 3H), 7.29-7.19 (m, 2H), 6.4-0 (d, 1H), 6.24 (d, 1H), 5.89 (d, 1H), 5.73 (m, 1H), 5.71 (s, 1H), 5.43 (m, 1H), 5.12-5.07 (m, 2H), 4.32 (m, 1H), 4.21 (m, 2H), 4.14 (m, 2H), 2.82 (m, 1H), 2.69 (m, 4H), 2.27 (m, 4H), 1.83 (m, 6H), 1.70 (m, 3H), 1.63 (s, 6H), 1.62 (s, 6H), 1.53 (m, 6H), 1.38 (m, 6H), 1.23 (m, 4H), 1.14 (m, 4H), 1.01 (s, 1H), 0.97 (s, 6H), 0.77 (q, 2H), 0.67 (t, 3H). Mass spectrum (ESI) m/z 1105.58 [M+H]+.

Scheme 2. - Illustrative reaction scheme for the synthesis of DZ-SIM ester

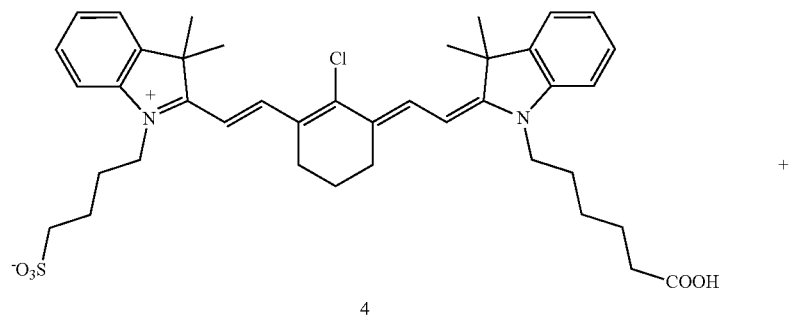

4

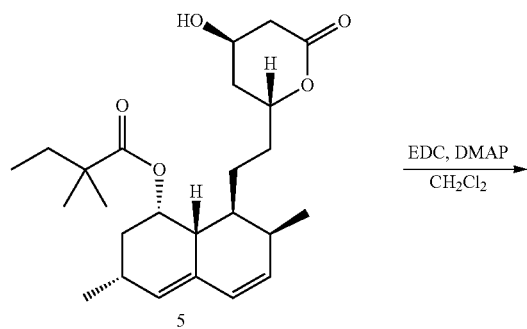

5

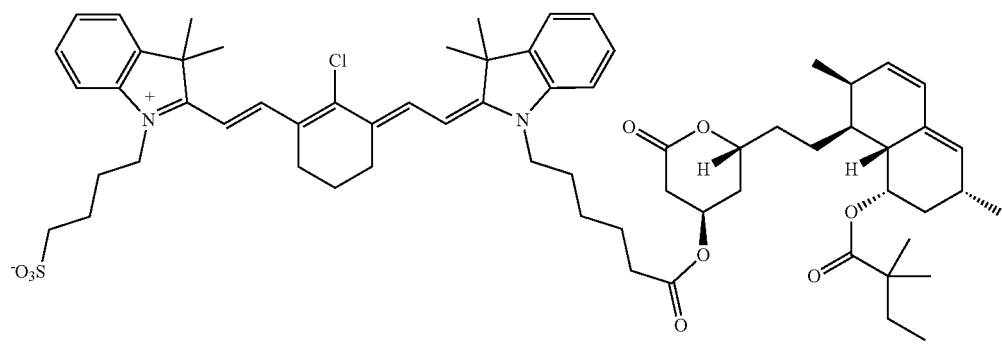

6

DZ-SIM amide may be synthesized as illustrated in the reaction scheme 3 below, e.g. as follows: To a solution of simvastatin 5 (1 g, 2.39 mmol, 1 eq.) in acetonitrile, propane-1,3-diamine (1 mL, 11.95 mmol, 5 eq.) was added. The mixture was refluxed with continuous stirring for 4 h. The solvent was removed under reduced pressure and the product was dried in high vacuum. The resulting product 7 was used without further purification. The mixture of DZ1 (500 mg, 0.71 mmol) 1-ethyl-3-(3-dimethyllaminopropyl) carbodiie hydrochloride (204 mg, 1.07 mmol) and 1-hydroxy-7-azabenzotriazole (115 mg, 0.85 mmol) were dissolved in 10.0 mL $CH_2Cl_2$ solution. The mixture was stirred for 15 min, then compound 7 (350 mg, 0.71 mmol) was added and stirred for additional 2 hours at rt. The solvent was removed under reduced pressure and the product was purified by C18-RP silica chromatography elution with methanol-water to afford desired product 8 as a dark green solid 327 mg (39%). Mass spectrum (ESI) 1179.65 [M+H]+.

Scheme 3-Illustrative reaction scheme for the synthesis of DZ-SIM amide.

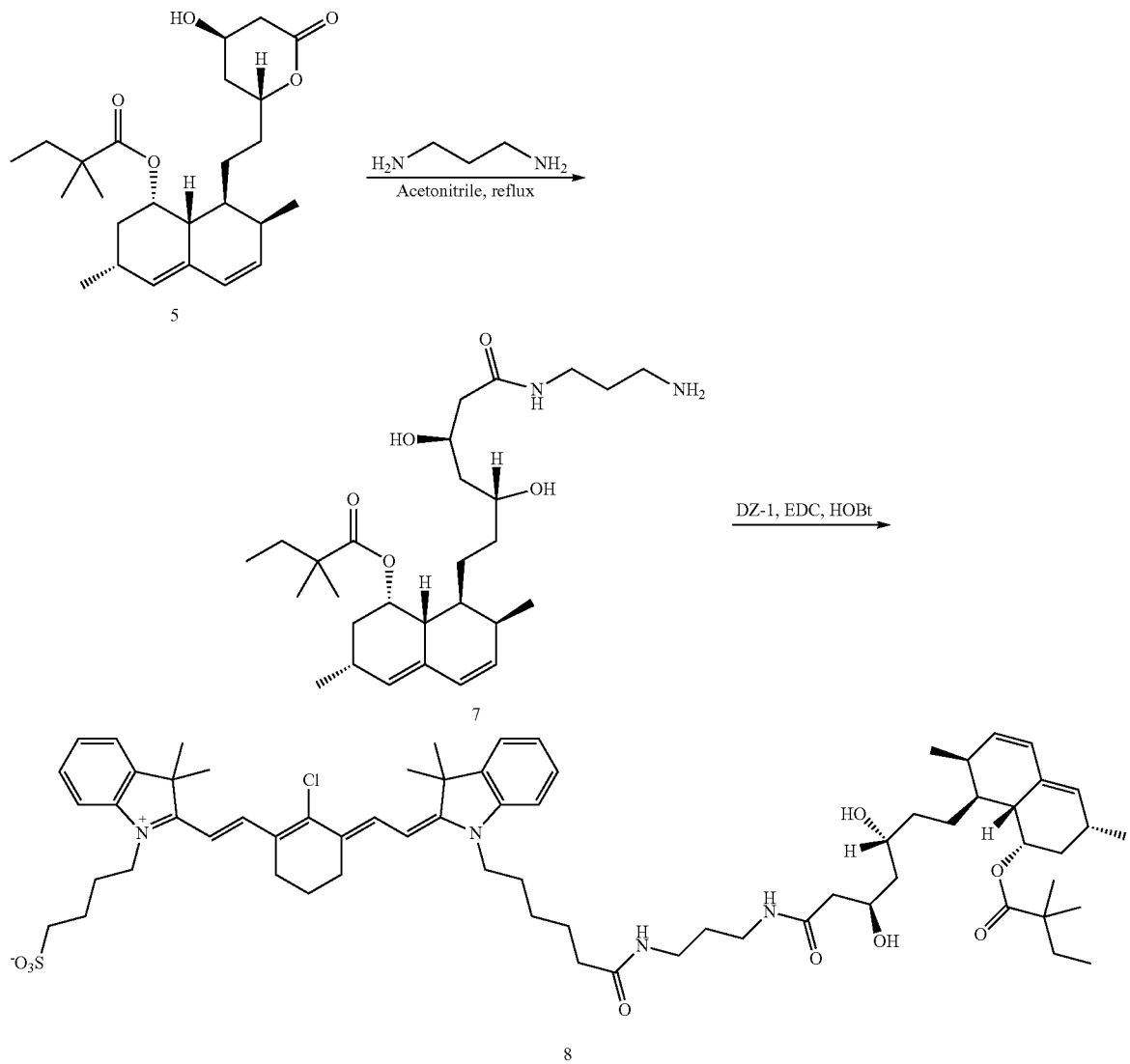

DZ-CIS-ester (11) may be synthesized as illustrated in the reaction scheme 4 below, e.g. as follows: Oxoplatin 10 was synthesized according to the literature method (Journal of Inorganic Biochemistry 107 (2012) 6-14). To a suspension of compound 10 (350 mg, 1.05 mmol) in DMSO (20 ml) was added DZ 1 (500 mg, 0.71 mmol) followed by 1-ethyl-3-(3-dimethyllaminopropyl) carbodiie hydrochloride (163 mg, 0.85) and DMAP (80 mg, 0.65 mmol) and the mixture was stirred for 20 h at room temperature to afford green solution. The solution was filtered and the DMSO was removed by lyophilization. The product was purified with C18-RP silica chromatography, elution with methanol-water to afford DZ-CIS 11 as a dark green solid (275 mg, yield 38%). Mass spectrum (ESI) 1020.69 (M+H)+.

1H NMR (DMSO-d6, 400 MHz) δ 8.22 (m, 2H), 7.61-7.56 (m, 2H), 7.48 (d, 1H), 7.39 (m, 3H), 7.26 (m, 2H), 6.37 (d, 1H), 6.24 (d, 1H), 4.15 (m, 4H), 2.68 (m, 4H), 2.15 (m, 2H), 1.80 (m, 4H), 1.70 (m, 6H), 1.63 (s, 6H), 1.62 (s, 6H), 1.51 (m, 2H), 1.40 (m, 2H). Mass spectrum (ESI) m/z 1020.69 (M+H)+.

Scheme 4-Illustrative reaction scheme for the synthesis of DZ-CIS ester.

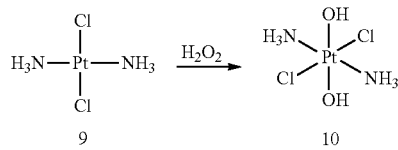

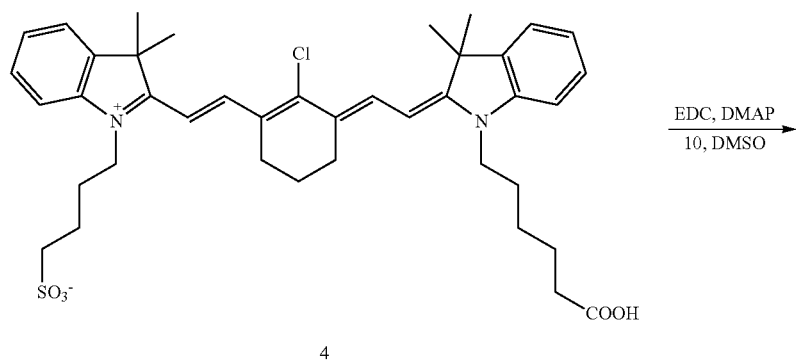

4

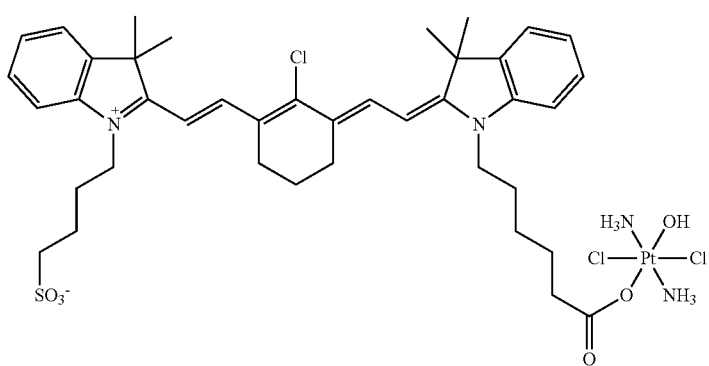

11

DZ-ART ester 13 may be synthesized as illustrated in the reaction scheme below, e.g. as follows: To a solution of dye 4 (250 mg, 0.35 mmol) in methylene chloride (20 ml) was added dihydroartemisinin 12 (110 mg, 0.39 mmol), 1-ethyl-3-(3-dimethyllaminopropyl) carbodiie hydrochloride (82 mg, 0.43) and DMAP (20 mg, 0.16 mmol) and the mixture was stirred 12 hours at room temperature to afford green solution. The solution was filtered and the solvent was removed under reduced pressure. DZ-ART was purified by C18-RP silica column chromatography elution with methanol-water to afford DZ-ART 13 as a dark green solid 179 mg (52%). 1H NMR (DMSO-d6, 400 MHz) δ 8.22 (m, 2H), 7.58 (m, 2H), 7.47 (d, 1H), 7.38 (m, 3H), 7.25 (m, 2H), 6.38 (d, 1H), 6.25 (d, 1H), 5.60 (d, 1H), 5.50 (s, 1H), 4.55 (m, 2H), 4.21 (m, 4H), 2.68 (m, 6H), 2.35 (m, 2H), 2.17 (m, 2H), 1.86 (m, 6H), 1.73 (m, 6H), 1.64 (s, 6H), 1.63 (s, 6H), 1.57 (m, 2H), 1.37 (m, 2H), 1.24 (m, 2H), 1.22 (s, 3H), 0.84 (m, 3H), 0.67 (m, 2H). Mass spectrum (ESI) m/z 971.46 [M+H]+.

Scheme 5. Synthesis of DZ-ART ester conjugate

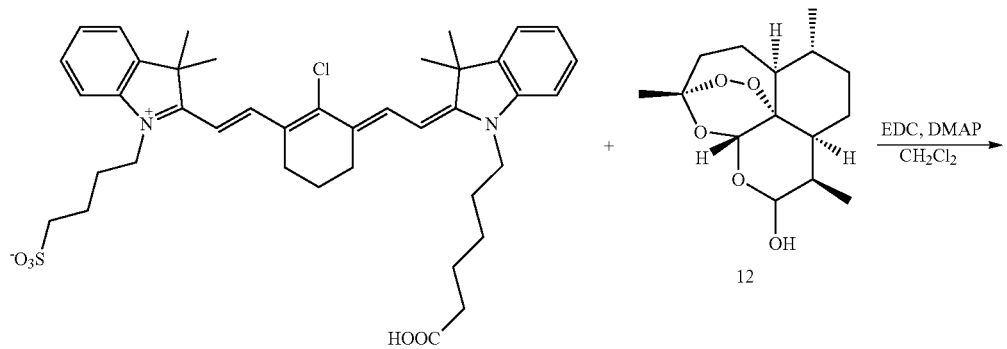

4

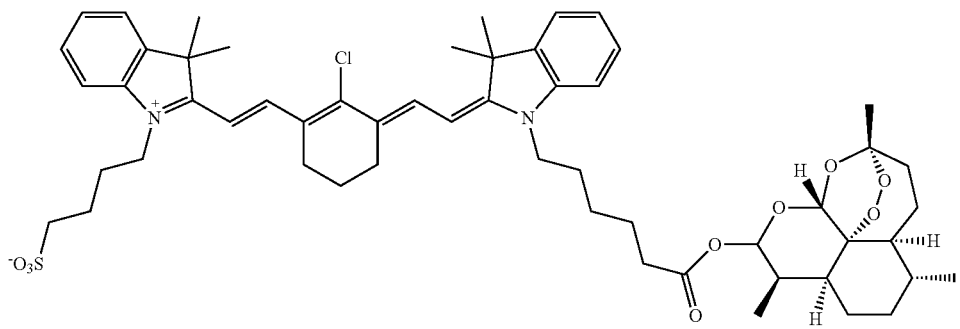

13

DZ-doxorubicin amide 15 may be synthesized as illustrated in the reaction scheme 6 below, e.g. as follows: The mixture of DZ 1 (103 mg, 0.15 mmol) 1-ethyl-3-(3-dimethylaminopropyl) carbodiie hydrochloride (40 mg, 0.21 mmol) and 1-hydroxy-7-azabenzotriazole (24 mg, 0.18 mmol) were dissolved in 5.0 ml DMF solution. The mixture was stirred for 15 min, then doxorubicin hydrochloride 14 (85 mg, 0.15 mmol) was added and stirred for additional 15 hours at RT. Ethyl ether (50 ml) was added. The precipitate collected and purified by C18-RP silica chromatography elution with methanol-water to afford desired product 15 as a dark green solid 83 mg (46%). 1H NMR (DMSO-d6, 400 MHz) δ 8.18 (m, 2H), 7.90 (m, 2H), 7.62 (m, 2H), 7.49 (m, 2H), 7.41 (m, 2H), 7.32 (s, 1H), 7.29 (m, 1H), 7.25 (m, 1H), 6.37 (d, 1H), 6.24 (d, 1H), 5.45 (s, 1H), 5.18 (s, 1H), 4.92 (m, 1H), 4.80 (m, 1H), 4.67 (m, 1H), 4.52 (m, 2H), 4.21 (m, 2H), 4.11 (m, 2H), 3.93 (s, 3H), 2.96 (s, 1H), 2.63 (m, 4H), 2.15 (m, 2H), 2.00 (m, 4H), 1.76 (m, 6H), 1.64 (s, 6H), 1.63 (s, 6H), 1.56 (s, 3H), 1.55 (s, 3H), 1.48 (m, 2H), 1.20 (m, 2H), 1.08 (m, 2H). Mass spectrum (ESI) m/z 1230.47 [M+H]+.

Scheme 6. Synthesis of DZ-1-Dox amide conjugate

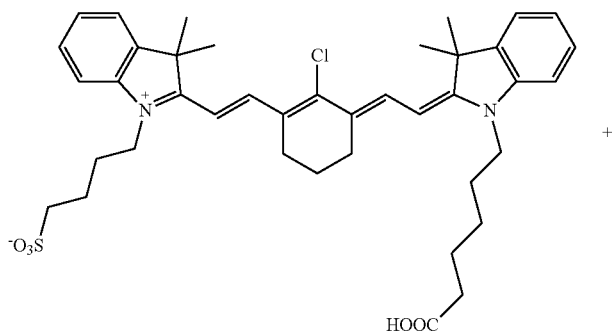

4

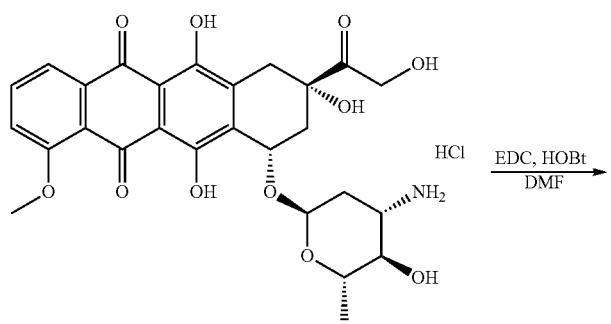

14

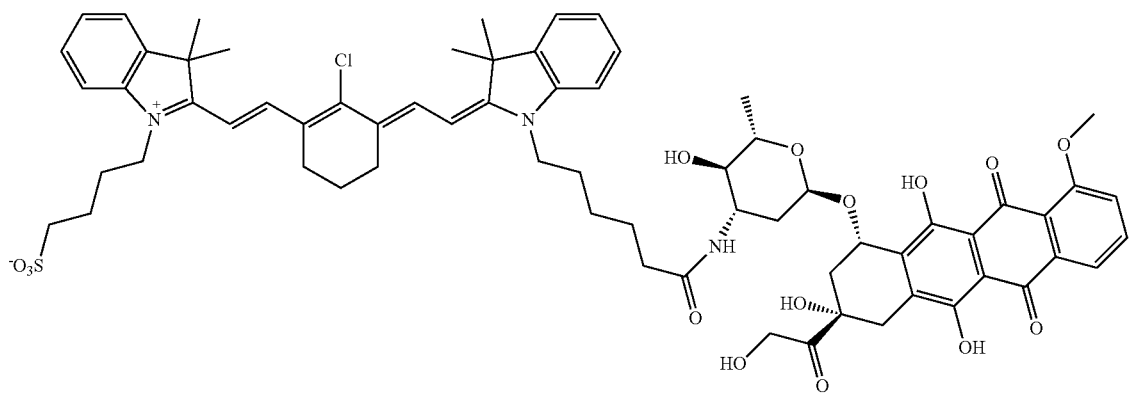

15

While multiple embodiments are disclosed, still other embodiments of the present invention will become apparent to those skilled in the art from this detailed description. There may be aspects of this invention that may be practiced without the implementation of some features as they are described. It should be understood that some details have not been described in detail in order to not unnecessarily obscure the focus of the invention. The invention is capable of myriad modifications in various obvious aspects, all without departing from the spirit and scope of the present invention. Accordingly, the drawings and descriptions are to be regarded as illustrative rather than restrictive in nature.

The invention claimed is:

1. A method of sensitizing cancer or precancerous cells present in a subject to the treatment with a tyrosine kinase inhibitor (TKI), the method comprising administering to a subject in need of TKI treatment:
   a TKI in an amount and concentration sufficient to cause a cancer cell growth inhibiting and/or apoptosis-inducing TKI effect when administered to the subject together with, or in presence of, one or more sensitizer compound, wherein the TKI is not conjugated to the sensitizer compound; and
   a sensitizer compound, in an amount and concentration sufficient to provide cancer cell sensitivity to the tyrosine kinase inhibitor, thus allowing for an enhanced effect of the TKI compared to a TKI administered in absence of the sensitizer compound;
wherein the cancer or precancerous cells are of a cancer that develops TKI resistance, the cancer that develops TKI resistance comprising: a cancer that is associated with tyrosine kinase abnormalities, a cancer which overexpresses a tyrosine kinase, and a cancer associated with mutations that lead to EGFR overexpression;
wherein the sensitizer compound is a DZ1-drug amide or ester conjugate comprising a drug residue,
and wherein the drug forming the drug residue is selected from the group consisting of a statin drug, a platin-based anti-neoplastic drug, and artemisinin, and wherein the DZ1 residue is selected from an amide and an ester-linked residue shown in formulae FI and FII below:

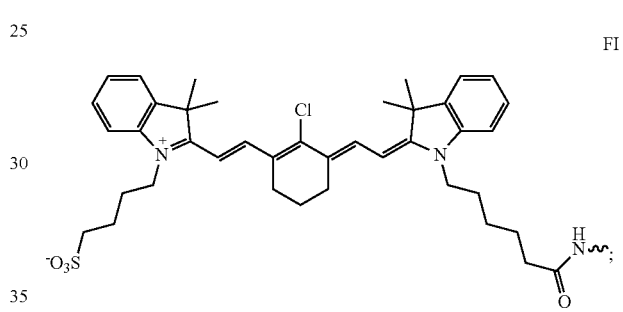

wherein ~ represents a point of attachment to the drug residue.

2. The method of claim 1, wherein the drug is a statin selected from the group consisting of atorvastatin, fluvastatin, lovastatin, pitavastatin, pravastatin, and rosuvastatin.

3. The method of claim 1, wherein the drug is selected from an ester- or amide-conjugated Simvastatin (SIM), Cisplatin (CIS), and Artemisinin (ART).

4. The method of claim 1, wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

5. The method of claim 1, wherein the tyrosine kinase inhibitor is selected from the group consisting of Gefitinib and Icotinib.

6. The method of claim 1, comprising administering one or more combination selected from the group consisting of:
Gefitinib in combination with a DZ1-SIM ester sensitizer;
Gefitinib in combination with a DZ1-SIM amide sensitizer;
Gefitinib in combination with a DZ1-CIS ester sensitizer;
Gefitinib in combination with a DZ1-CIS amide sensitizer;
Gefitinib in combination with a DZ1-ART ester sensitizer;
Gefitinib in combination with a DZ1-ART amide sensitizer.

7. The method of claim 1, comprising administering one or more combination selected from the group consisting of:
Icotinib in combination with a DZ1-SIM ester sensitizer;
Icotinib in combination with a DZ1-SIM amide sensitizer;
Icotinib in combination with a DZ1-CIS ester sensitizer; and/or
Icotinib in combination with a DZ1-CIS amide sensitizer;
Icotinib in combination with a DZ1-ART ester sensitizer; and/or
Icotinib in combination with a DZ1-ART amide sensitizer.

8. The method of claim 1, comprising administering one or more combination selected from the group consisting of:
Everolimus in combination with a DZ1-SIM ester sensitizer;
Everolimus in combination with a DZ1-SIM amide sensitizer;
Everolimus in combination with a DZ1-CIS ester sensitizer;
Everolimus in combination with a DZ1-CIS amide sensitizer;
Everolimus in combination with a DZ1-ART ester sensitizer; and/or
Everolimus in combination with a DZ1-ART amide sensitizer.

9. The method of claim 1, comprising administering one or more TKI selected from the group consisting of Gefitinib, Icotinib, Erlotinib, Afatinib, Brigatinib, Osimertinib, Dacomitinib, Everolimus, and Lapatinib, in combination with or presence of a sensitizer compound selected from the group consisting of:
a DZ1-SIM ester sensitizer;
a DZ1-SIM amide sensitizer;
a DZ1-CIS ester sensitizer; and
a DZ1-CIS amide sensitizer:
a DZ1-ART ester sensitizer; and
a DZ1-ART amide sensitizer.

10. The method of claim 1, wherein the cancer or precancerous cells is selected from cells of one or more of lung cancer, NSCLC, SCLC, pancreatic cancer, colorectal cancer, prostate cancer, skin cancer, HCC cancer, and breast cancer, squamous-cell carcinoma of the lung, anal cancers, glioblastoma, and epithelial tumors of the head and neck.

11. A method of providing a kit, the method comprising:
(1) providing one or more sensitizer compound in a suitable form for delivery, wherein the sensitizer compound is a DZ1-drug amide or ester conjugate comprising a DZ1 residue and a drug residue,
(2) providing at least one pharmaceutically acceptable carrier, and
(3) providing instructions for coordinated administration of the sensitizer compound and a tyrosine kinase inhibitor (TKI), wherein the TKI is not conjugated to the sensitizer compound, in a common administration regimen for treatment of a cancer that develops TKI resistance;

wherein the cancer that develops TKI resistance comprises: a cancer that is associated with tyrosine kinase abnormalities, a cancer which overexpresses a tyrosine kinase, and a cancer associated with mutations that lead to EGFR overexpression; wherein the drug forming the drug residue of the sensitizer is selected from the group consisting of a statin drug, a platin-based anti-neoplastic drug, and artemisinin, and wherein the DZ1 residue is selected from an amide and an ester-linked residue shown in formulae I and II below:

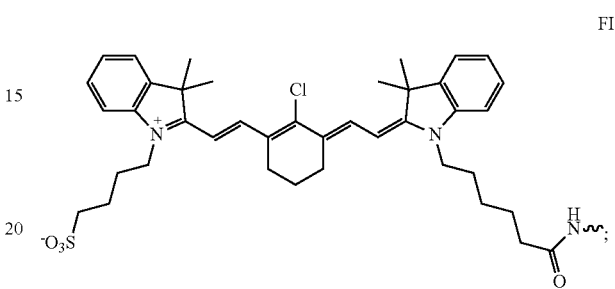

FI

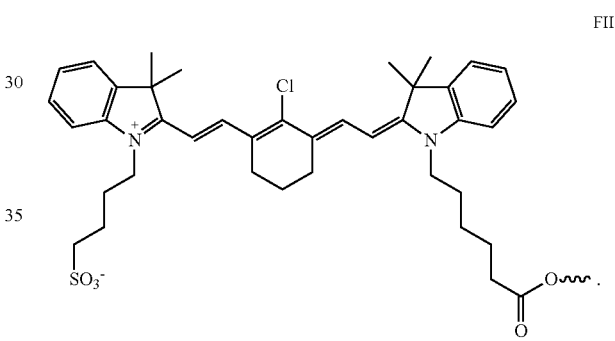

FII wherein ~ represents a point of attachment to the drug residue.

12. The method of claim 11, wherein the kit further comprises (4) a tyrosine kinase inhibitor (TKI) in a suitable form for delivery.

13. The method of claim 11, wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

14. The method of claim 12, wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

15. The method of claim 11, wherein the TKI is selected from the group consisting of Gefitinib and Icotinib, wherein the sensitizer compound comprises a conjugated drug selected from the group of Simvastatin (SIM), Cisplatin (CIS), and Artemisinin (ART), and the sensitizer compound is selected from the group consisting of DZ1-SIM ester, DZ1-SIM amide, DZ1-CIS ester, DZ1-CIS amide, DZ1-ART ester, and DZ1-ART amide.

16. The method of claim 11, wherein the concentration of the sensitizer compound and its carrier are adapted to deliver the sensitizer to pre-cancerous, cancer or tumor cells of a TKI associated tumor in sufficient concentration to sensitize the cells against a TKI.

17. A kit, the kit comprising:
(1) one or more sensitizer compound in a suitable form for delivery, wherein the sensitizer compound is a DZ1-drug amide or ester conjugate comprising a DZ1 residue and a drug residue,
(2) at least one pharmaceutically acceptable carrier, and
(3) instructions for coordinated administration of the sensitizer compound and a tyrosine kinase inhibitor (TKI), wherein the TKI is not conjugated to the sensitizer compound, in a common administration regimen for treatment of a cancer that develops TKI resistance;

wherein the cancer that develops TKI resistance comprises: a cancer that is associated with tyrosine kinase abnormalities, a cancer which overexpresses a tyrosine kinase, and a cancer associated with mutations that lead to EGFR overexpression; wherein the drug forming the drug residue of the sensitizer is selected from the group consisting of a statin drug, a platin-based anti-neoplastic drug, and artemisinin, and wherein the DZ1 residue is selected from an amide and an ester-linked residue shown in formulae I and II below:

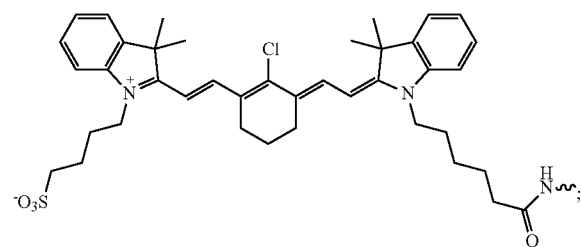

FI

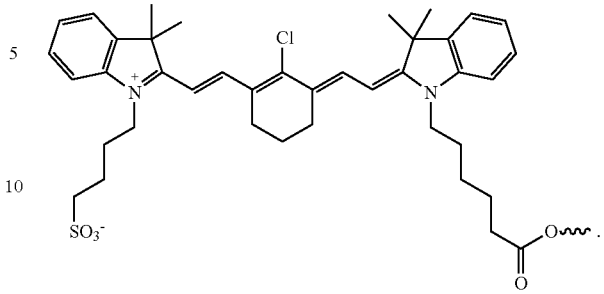

FII wherein ~ represents a point of attachment to the drug residue.

18. The kit of claim 17, wherein the kit further comprises (4) a tyrosine kinase inhibitor (TKI) in a suitable form for delivery.

19. The kit of claim 17, wherein the tyrosine kinase inhibitor is selected from the group consisting of Gefitinib, Icotinib, Erlotinib, Afatinib, Brigatinib, Osimertinib, Dacomitinib, Everolimus, and Lapatinib.

20. The kit of claim 17, wherein the TKI is selected from the group consisting of Gefitinib and Icotinib, wherein the sensitizer compound comprises a conjugated drug selected from the group of Simvastatin (SIM), Cisplatin (CIS), and Artemisinin (ART), and the sensitizer compound is selected from the group consisting of DZ1-SIM ester, DZ1-SIM amide, DZ1-CIS ester, DZ1-CIS amide, DZ1-ART ester, and DZ1-ART amide.

21. The kit of claim 17, wherein the concentration of the sensitizer compound and its carrier are adapted to deliver the sensitizer to pre-cancerous, cancer or tumor cells of a TKI associated tumor in sufficient concentration to sensitize the cells against a TKI.

* * * * *